(12) United States Patent
Sweeney et al.

(10) Patent No.: US 7,906,540 B2
(45) Date of Patent: Mar. 15, 2011

(54) NON-NUCLEOSIDE REVERSE TRANSCRIPTASE INHIBITORS

(75) Inventors: Zachary Kevin Sweeney, Redwood City, CA (US); Michael Welch, Mountain View, CA (US)

(73) Assignee: Roche Palo Alto LLC, South San Francisco, CA (US)

(*) Notice: Subject to any disclaimer, the term of this patent is extended or adjusted under 35 U.S.C. 154(b) by 50 days.

(21) Appl. No.: 12/079,649

(22) Filed: Mar. 28, 2008

(65) Prior Publication Data

US 2008/0249151 A1   Oct. 9, 2008

Related U.S. Application Data

(60) Provisional application No. 60/920,635, filed on Mar. 29, 2007.

(51) Int. Cl.
*A61K 31/4196* (2006.01)
*C07D 249/12* (2006.01)

(52) U.S. Cl. ............ 514/384; 548/263.2; 548/263.4
(58) Field of Classification Search .......... 514/383; 548/262.2

See application file for complete search history.

(56) References Cited

U.S. PATENT DOCUMENTS

| | | |
|---|---|---|
| 3,274,185 A | 9/1966 | Sigal et al. |
| 3,813,384 A | 5/1974 | Vogelsang et al. |
| 4,826,990 A | 5/1989 | Musser et al. |
| 4,942,236 A | 7/1990 | Musser et al. |
| 5,103,014 A | 4/1992 | Musser et al. |
| 5,331,002 A | 7/1994 | Miller |
| 5,436,252 A | 7/1995 | Sorensen et al. |
| 6,140,499 A | 10/2000 | Fortunak et al. |
| 6,248,769 B1 | 6/2001 | Cavalla et al. |

FOREIGN PATENT DOCUMENTS

| | | | |
|---|---|---|---|
| EP | 0 435 177 B1 | 7/1991 | |
| EP | 0 273 309 B1 | 1/1995 | |
| EP | 0 273 310 B1 | 6/1995 | |
| JP | 60 215675 | 10/1985 | |
| JP | 60215675 | * 10/1985 | ............ 548/262.2 |
| WO | WO 96/13264 A1 | 5/1996 | |
| WO | WO 97/40017 A2 | 10/1997 | |
| WO | WO 98/04135 A1 | 2/1998 | |
| WO | WO 02/38553 A2 | 5/2002 | |
| WO | WO 2004/074257 A1 | 9/2004 | |
| WO | WO 2004/085406 A1 | 10/2004 | |
| WO | WO 2005/102989 A1 | 11/2005 | |
| WO | WO 2006/010545 A1 | 2/2006 | |

OTHER PUBLICATIONS

Patini et al, Chem. Rev., 96(8), 1996, pp. 3147-3176, esp. p. 3149.*
Translation of JP 60215675, Oct. 1985, Akita et al., see pp. 17-19 in particular.*
Buckheit, R. W., Jr. "Non-Nucleoside reverse transcriptase inhibitors: perspectives on novel therapeutic compounds and strategies for the treatment of HIV infection," *Expert Opinion* (2001) vol. 10 (8) p. 1423-1442.
De Clercq, E. "New Developments in Anti-HIV Chemotherapy," *Current Medicinal Chemistry* (2001) vol. 8, p. 1543-1572.
Del Olmo, E. et. al. "Anti-Trypanosoma Activity of Some Natural Stilbenoids and Synthesis Related Heterocyclic Compounds," *Bioorganic & Med. Chem. Lett.* (2001) vol. 11, p. 2755-2757.
Rosen G. H., et. al. "2-Benzyl-1,3,4-oxadiazolin-5-one and related compounds," *Journal of Heterocyclic Chemistry* (1971) p. 659-662.
Wilder Smith, A.E. "Preparation of some New 4-Substituted Derivatives of p-Amino-o-hydroxy-phenyl-1,3,4-oxadizolone-5 and Study of their Mycobacteriostatic Properties," *Arzneim-forschung* (1967) vol. 67 (17), p. 768-772.
Yuksek, H., et. al. "Synthesis and Antibacterial Activities of some 4,5-Dihydro-1H-1,2,4-triazol-5-ones," *Arzneim-forschung* (1997) vol. 47 (4), p. 405-409.

* cited by examiner

*Primary Examiner* — Yong Chu
*Assistant Examiner* — Michael Barker
(74) *Attorney, Agent, or Firm* — Brian L. Buckwalter

(57) ABSTRACT

Compounds of formula I, wherein $R^1$, $R^2$, $R^3$, $R^4$, $R^5$, X, Y, and Ar are as defined herein or pharmaceutically acceptable salts thereof, inhibit HIV-1 reverse transcriptase and afford a method for prevention and treatment of HIV-1 infections and the treatment of AIDS and/or ARC. The present invention also relates to compositions containing compounds of formula I useful for the prevention and treatment of HIV-1 infections and the treatment of AIDS and/or ARC.

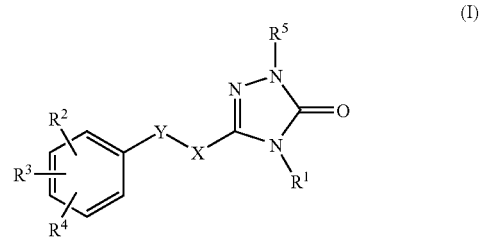

(I)

14 Claims, No Drawings

NON-NUCLEOSIDE REVERSE TRANSCRIPTASE INHIBITORS

CROSS REFERENCE TO PRIOR APPLICATIONS

This application is claims benefit of U.S. Provisional Application No. 60/920,635, filed Mar. 29, 2007, which is hereby incorporated by reference in its entirety.

FIELD OF THE INVENTION

The invention relates to the field of antiviral therapy and, in particular, to non-nucleoside compounds that inhibit HIV-1 reverse transcriptase and are useful for treating Human Immunodeficiency Virus (HIV) mediated diseases. The invention provides novel triazolone compounds according to formula I, for treatment or prophylaxis of HIV mediated diseases, AIDS or ARC, employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the CD4+ T-cell, with attendant susceptibility to opportunistic infections. HIV infection is also associated with a precursor AIDS—related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase. (J. S. G. Montaner et al., *Antiretroviral therapy: 'the state of the art' Biomed & Pharmacother.* 1999 53:63-72; R. W. Shafer and D. A. Vuitton, *Highly active retroviral therapy (HAART) for the treatment of infection with human immunodeficiency virus type, Biomed. & Pharmacother.* 1999 53 :73-86; E. De Clercq, *New Developments in Anti-HIV Chemotherap. Curr. Med. Chem.* 2001 8:1543-1572). Two general classes of RTI inhibitors have been identified: nucleoside reverse transcriptase inhibitors (NRTI) and non-nucleoside reverse transcriptase inhibitors. Currently the CCR5 co-receptor has emerged as a potential target for anti-HIV chemotherapy (D. Chantry, *Expert Opin. Emerg. Drugs* 2004 9(1):1-7; C. G. Barber, *Curr. Opin. Invest. Drugs* 2004 5(8):851-861; D. Schols, *Curr. Topics Med. Chem.* 2004 4(9):883-893; N. A. Meanwell and J. F. Kadow, *Curr. Opin. Drug Discov. Dev.* 2003 6(4):451-461). N-substituted hydroxy pyrimidinone carboxamide inhibitors of HIV-1 integrase inhibitors have been disclosed by B. Crescenzi et al. in WO2003/035077, published May 1, 2003, and MK-0518 (raltegravir) has been approved by the FDA.

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTIs are allosteric inhibitors which bind reversibly at a nonsubstrate-binding site on the HIV reverse transcriptase thereby altering the shape of the active site or blocking polymerase activity (R. W. Buckheit, Jr., *Non-nucleoside reverse transcriptase inhibitors: perspectives for novel therapeutic compounds and strategies for treatment of HIV infection, Expert Opin. Investig. Drugs* 2001 10(8)1423-1442; E. De Clercq, *The role of non-nucleoside reverse transcriptase inhibitors (NNRTIs) in the therapy of HIV infection, Antiviral Res.* 1998 38:153-179; E. De Clercq, *New Developments in Anti-HIV Chemotherapy, Current medicinal Chem.* 2001 8(13):1543-1572; G. Moyle, *The Emerging Roles of Non-Nucleoside Reverse Transcriptase Inhibitors in Antiviral Therapy*, Drugs 2001 61 (1): 19-26). Although over thirty structural classes of NNRTIs have been identified in the laboratory, only four compounds have been approved for HIV therapy: efavirenz, nevirapine, delavirdine and etravirine.

Initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT. While combination therapy with NRTIs, PIs and NNRTIs has, in many cases, dramatically lowered viral loads and slowed disease progression, significant therapeutic problems remain. (R. M. Gulick, *Eur. Soc. Clin. Microbiol. and Inf. Dis.* 2003 9(3): 186-193) The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV.

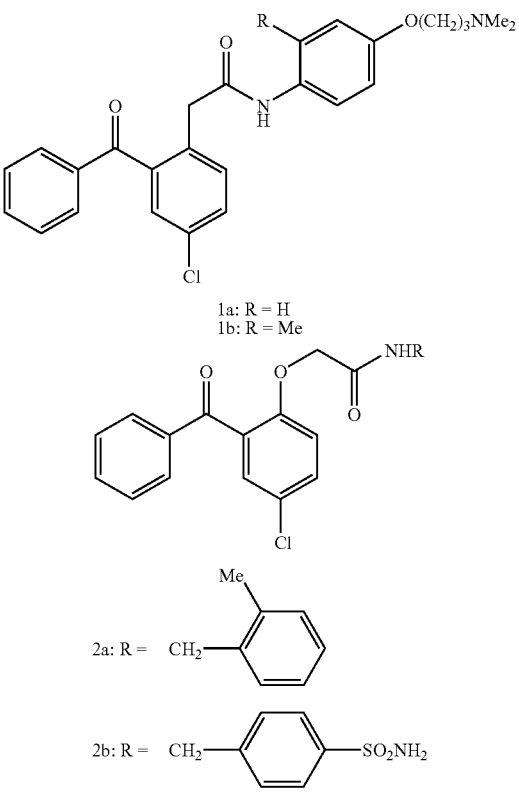

1a: R = H
1b: R = Me

2a: R = CH₂—(o-methylphenyl)

2b: R = CH₂—(p-SO₂NH₂-phenyl)

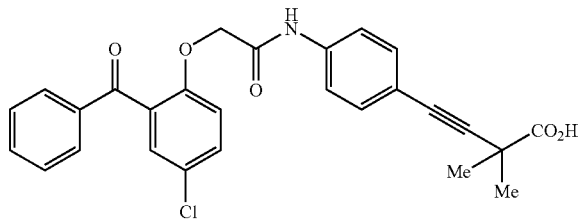

2-Benzoyl phenyl-N-[phenyl]-acetamide compounds 1a and 1b have been shown to inhibit HIV-1 reverse transcriptase (P. G. Wyatt et al., *J. Med. Chem.* 1995 38(10):1657-1665). Further screening identified related compounds, e.g. 2-benzoyl phenyloxy-N-[phenyl]-acetamide, 2a, and a sulfonamide derivative 2b which also inhibited reverse transcriptase (J. H. Chan et al., *J Med. Chem.* 2004 47(5): 1175-1182; K. Romimes et al., *J. Med. Chem.* 2006 49(2):727-739; C. L. Webster et al., WO01/17982). P. Bonneau et al. in US 20060069261 published Mar. 30, 2006 disclose 4-{4-[2-(2-benzoyl-phenoxy)-acetylamino]-phenyl}-2,2-dimethyl-but-3-ynoic acid compounds 3 which are inhibitors of HIV reverse transcriptase.

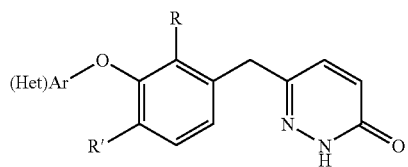

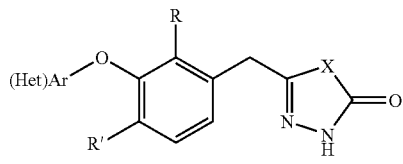

5: X = NH, O, S

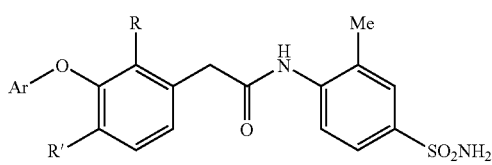

R = hydrogen, halogen
R' = chloro, bromo, alkyl, cycloalkyl alkoxy

Pyridazinone non-nucleoside reverse transcriptase inhibitors 4 have been described by J. P. Dunn et al. in U.S. Publication filed Mar. 23, 2004 and by J. P. Dunn et al. in U.S. Publication No. 2005021554 filed Mar. 22, 2005. 5-Aralkyl-2,4-dihydro-[1,2,4]triazol-3-one, 5-aralkyl-3H-[1,3,4]oxadiazol-2-one and 5-aralkyl-3H-[1,3,4]thiadiazol-2-one non-nucleoside reverse transcriptase inhibitors 5 have been disclosed by J. P. Dunn et al. in U.S. Publication No. 20040192704 filed Mar. 23, 2004 and by J. P. Dunn et al. in U.S. Publication No. 20060025462 filed Jun. 27, 2005. Related compounds are disclosed by Y. D. Saito et al. in U.S. Pub. No. 20070078128 filed Sep. 29, 2006. Phenylacetamide non-nucleoside reverse transcriptase inhibitors 6 have been disclosed by J. P. Dunn et al. in U.S. Pub. No. 20050239881 published Oct. 27, 2005 and methods for treating retroviral infection with phenylacetamide compounds have been disclosed by J. P. Dunn et al. in U.S. Publication No. 20050239880 published Oct. 27, 2005; T. Mirzadegan and T, Silva in U.S. Publication No. 20070088015 filed Oct. 18, 2006; and Z. K. Sweeney and T. Silva in U.S. Publication No 20070088053 Oct. 18, 2006. These applications are hereby incorporated by reference in their entirety.

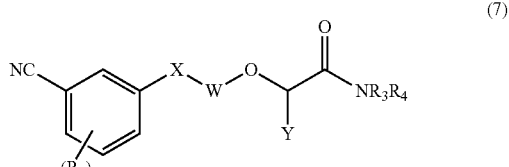

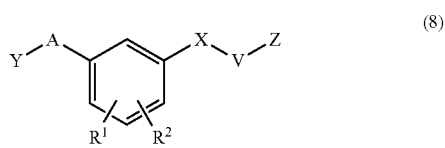

In WO2006/067587 published Jun. 26, 2006, L. H. Jones et al. disclose biaryl ether derivatives 7 and compositions containing them which bind to the enzyme reverse transcriptase and are modulators, especially inhibitors, thereof. In U.S. Patent Publication 2007/0021442 published Jan. 25, 2007, S. A. Saggar et al. disclose HIV reverse transcriptase inhibitors of formula 8.

SUMMARY OF THE INVENTION

The present invention relates to a compound according to formula I

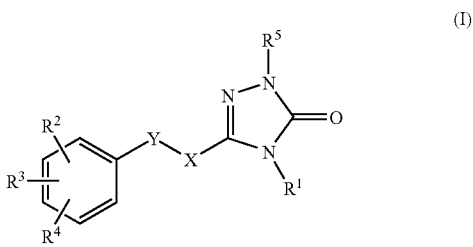

wherein:
X is $CH_2$ or NH;
Y is $CH_2$ or O with the proviso that at least one of X or Y is $CH_2$;
$R^1$ is hydrogen or $C_{1-6}$ alkyl;
$R^2$ is C(=O)Ar or OAr;
$R^3$ and $R^4$ are independently hydrogen, halogen, $C_{1-6}$ alkyl, $C_{1-6}$ alkoxy or $C_{3-5}$ cycloalkyl;
$R^5$ is hydrogen, $CH_2OH$, $CH_2OC(=O)(CH_2)_nC(=O)OH$, $CH_2OC(=O)C_{1-6}$ alkyl where n is 2 to 5, or $CH_2OC(=O)CHR^{5a}NH_2$ where $R^{5a}$ is phenyl or $C_{1-6}$ lower alkyl;
Ar is phenyl substituted with 1 to 3 groups independently selected from halogen, cyano, $C_{1-6}$ haloalkyl, $C_{3-5}$ cycloalkyl or $C_{1-6}$ alkyl; or,
pharmaceutically acceptable salts thereof.

Compounds of formula I inhibit HIV-1 reverse transcriptase and afford a method for prevention and treatment of HIV-1 infections and the treatment of AIDS and/or ARC. HIV-1 undergoes facile mutations of its genetic code resulting in strains with reduced susceptibility to therapy with current therapeutic options. The present invention also relates to compositions containing compounds of formula I useful for the prevention and treatment of HIV-1 infections and the treatment of AIDS and/or ARC. The present invention further relates to compounds of formula I which are useful in mono therapy or combination therapy with other anti-viral agents.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The phrase "optional bond" means that the bond may or may not be present, and that the description includes single, double, or triple bonds. If a substituent is designated to be a "bond" or "absent", the atoms linked to the substituents are then directly connected.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such combinations result in stable compounds.

Unless expressly stated to the contrary, all ranges cited herein are inclusive. For example, a heterocyclic ring described as containing "1 to 4 heteroatoms" means the ring can contain 1, 2, 3 or 4 heteroatoms. It is also to be understood that any range cited herein includes within its scope all of the subranges within that range. Thus, for example, an aryl or a heteroaryl described as optionally substituted with "from 1 to 5 substituents" is intended to include as aspects thereof, any aryl optionally substituted with 1 to 4 substituents, 1 to 3 substituents, 1 to 2 substituents, 2 to 5 substituents, 2 to 4 substituents, 2 to 3 substituents, 3 to 5 substituents, 3 to 4 substituents, 4 to 5 substituents, 1 substituent, 2 substituents, 3 substituents, 4 substituents, and 5 substituents]

The symbols "*" at the end of a bond or "—" drawn through a bond each refer to the point of attachment of a functional group or other chemical moiety to the rest of the molecule of which it is a part. Thus, for example:

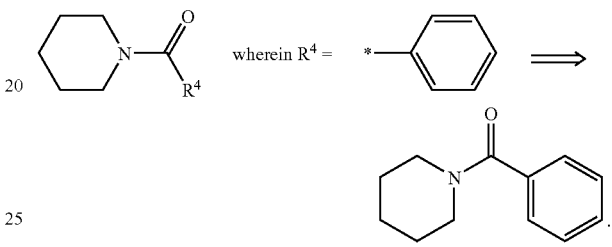

It is contemplated that the definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

In one embodiment of the present invention there is provided a compound according to formula I wherein $R^1$, $R^2$, $R^3$, $R^4$, $R^5$, X and Y are as defined herein above with the proviso that at least one of X or Y is $CH_2$.

In another embodiment of the present invention there is provided a compound according to formula I wherein $R^2$ is C(=O)Ar or OAr; Ar is phenyl substituted with 1 to 3 groups independently selected from halogen, cyano, $C_{1-6}$ haloalkyl or $C_{1-6}$ alkyl; and, $R^1$, $R^3$, $R^4$, $R^5$, X and Y are as defined herein above with the proviso that at least one of X or Y is $CH_2$.

In yet another embodiment of the present invention there is provided a compound according to formula I wherein X is $CH_2$ and, $R^1$, $R^2$, $R^3$, $R^4$, $R^5$ and Y are as defined herein above. In still another embodiment of the present invention there is provided a compound according to formula I selected from compounds I-1 to I-21 in TABLE I.

In a second embodiment of the present invention there is provided a compound according to formula IIa wherein $R^1$, $R^3$, $R^4$, $R^5$, Ar, X and Y are as defined herein above.

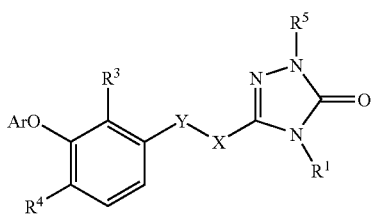
(IIa)

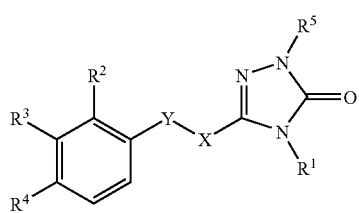
(IIb)

In a third embodiment of the present invention there is provided a compound according to formula IIa wherein X is $CH_2$, $R^3$ is fluoro; $R^4$ is halogen, $C_{1-6}$ alkyl or $C_{3-5}$ cycloalkyl; $R^5$ is hydrogen; and Ar and Y are as defined herein above.

In still another embodiment of the present invention there is provided a compound according to formula IIa wherein $R^3$ is fluoro; $R^4$ is halogen, $C_{1-6}$ alkyl, $C_{1-6}$ alkoxy or $C_{3-5}$ cycloalkyl; X is $CH_2$; $R^5$ is hydrogen, $CH_2OH$, $CH_2OC(=O)(CH_2)_nC(=O)OH$ or $CH_2OC(=O)C_{1-6}$ alkyl where n is 2 to 5; and $R^1$, Y and Ar are as defined herein above.

In a fourth embodiment of the present invention there is provided a compound according to formula IVa wherein $R^3$ is fluoro; $R^4$ is halogen, $C_{1-6}$ alkyl or $C_{3-5}$ cycloalkyl; $R^5$ is hydrogen; $R^7$ is halogen, cyano, $C_{3-5}$ cycloalkyl or $C_{1-6}$ haloalkyl.

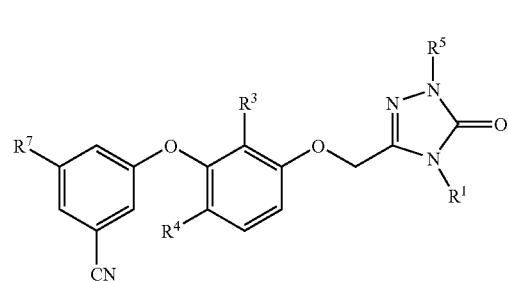
(IVa)

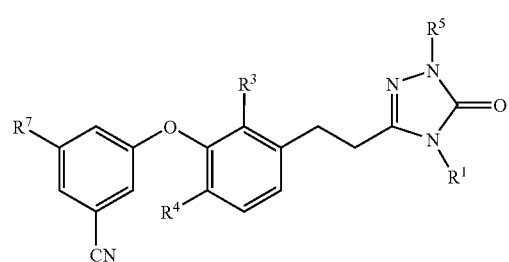
(IVb)

In another embodiment of the present invention there is provided a compound according to formula IVa wherein $R^3$ is fluoro; $R^4$ is halogen, $C_{1-6}$ alkyl or $C_{3-5}$ cycloalkyl; $R^5$ is $CH_2OH$, $CH_2OC(=O)(CH_2)_nC(=O)OH$ or $CH_2OC(=O)$ $C_{1-6}$ alkyl where n is 2 to 5; $R^7$ is halogen, cyano, $C_{3-5}$ cycloalkyl or $C_{1-6}$ haloalkyl.

In still another embodiment of the present invention there is provided a compound according to formula IVa wherein $R^3$ is fluoro; $R^4$ is halogen, $C_{1-6}$ alkyl or $C_{3-5}$ cycloalkyl; $R^5$ is $CH_2OC(=O)(CH_2)_nC(=O)OH$ where n is 2 to 5; $R^7$ is halogen, cyano or $C_{1-6}$ haloalkyl.

In a fifth embodiment of the present invention there is provided a compound according to formula IVb wherein $R^3$ is fluoro; $R^4$ is halogen, $C_{1-6}$ alkyl or $C_{3-5}$ cycloalkyl; $R^5$ is hydrogen; and, $R^7$ is halogen, cyano or $C_{1-6}$ haloalkyl.

In sixth embodiment of the present invention there is provided a compound according to formula IVb wherein $R^3$ is fluoro; $R^4$ is halogen, $C_{1-6}$ alkyl, $C_{1-6}$ alkoxy or $C_{3-5}$ cycloalkyl; $R^5$ is $CH_2OC(=O)(CH_2)_nC(=O)OH$ where n is 2 to 5; and, $R^7$ is halogen, cyano, $C_{3-5}$ cycloalkyl or $C_{1-6}$ haloalkyl.

In a seventh embodiment of the present invention there is provided a compound according to formula IIb wherein $R^2$ is OAr; $R^3$ and $R^4$ are independently hydrogen, halogen or $C_{1-6}$ alkyl; and, $R^5$ is hydrogen.

In an embodiment of the present invention there is provided a compound according to formula IIb wherein $R^2$ is OAr; $R^3$ and $R^4$ are independently hydrogen, halogen or $C_{1-6}$ alkyl; and, $R^5$ is $CH_2OH$, $CH_2OC(=O)(CH_2)_nC(=O)OH$ or $CH_2OC(=O)C_{1-6}$ alkyl where n is 2 to 5.

In eighth embodiment of the present invention there is provided a compound according to formula IIb wherein $R^2$ is OAr; $R^3$ and $R^4$ are independently hydrogen, halogen or $C_{1-6}$ alkyl; $R^5$ is hydrogen; X is O; and, Y is $CH_2$.

In another embodiment of the present invention there is provided a compound according to formula IIb wherein $R^2$ is OAr; $R^3$ and $R^4$ are independently hydrogen, halogen or $C_{1-6}$ alkyl; $R^5$ is $CH_2OH$, $CH_2OC(=O)(CH_2)_nC(=O)OH$ or $CH_2OC(=O)C_{1-6}$ alkyl where n is 2 to 5; X is O; and, Y is $CH_2$.

In a ninth embodiment of the present invention there is provided a compound according to formula Va wherein $R^3$ and $R^4$ are independently hydrogen, halogen or $C_{1-6}$ alkyl; $R^7$ is halogen, cyano, $C_{3-5}$ cycloalkyl or $C_{1-6}$ haloalkyl; and $R^5$ is hydrogen.

In still another embodiment of the present invention there is provided a compound according to formula Va wherein $R^3$ and $R^4$ are independently hydrogen, halogen or $C_{1-6}$ alkyl; $R^7$ is halogen, cyano, $C_{3-5}$ cycloalkyl or $C_{1-6}$ haloalkyl; and $R^5$ is $CH_2OH$, $CH_2OC(=O)(CH_2)_nC(=O)OH$ or $CH_2OC(=O)$ $C_{1-6}$ alkyl where n is 2 to 5.

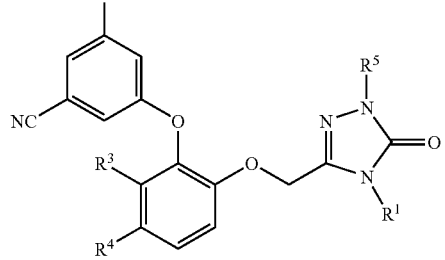
(Va)

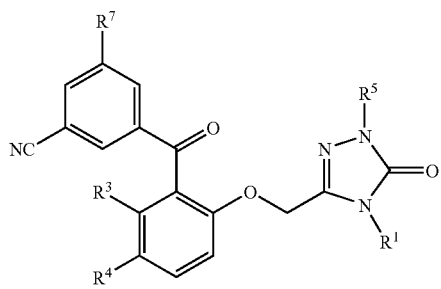

(Vb)

In tenth embodiment of the present invention there is provided a compound according to formula IIb wherein $R^2$ is C(=O)Ar; $R^3$ and $R^4$ are independently hydrogen, halogen or $C_{1-6}$ alkyl; X is $CH_2$; Y is O; and, $R^5$ is hydrogen.

In an eleventh embodiment of the present invention there is provided a compound according to formula Vb wherein $R^3$ and $R^4$ are independently hydrogen, halogen or $C_{1-6}$ alkyl; $R^7$ is halogen, cyano, $C_{3-5}$ cycloalkyl or $C_{1-6}$ haloalkyl; and $R^5$ is hydrogen.

In still another embodiment of the present invention there is provided a compound according to formula Vb wherein $R^3$ and $R^4$ are independently hydrogen, halogen or $C_{1-6}$ alkyl; $R^7$ is halogen, cyano, $C_{3-5}$ cycloalkyl or $C_{1-6}$ haloalkyl; $R^5$ is $CH_2OH$, $CH_2OC(=O)(CH_2)_nC(=O)OH$ or $CH_2OC(=O)$ $C_{1-6}$ alkyl where n is 2 to 5.

In a twelfth embodiment of the present invention there is provided a compound according to formula Vb wherein $R^3$ is halogen and $R^4$ are halogen or $C_{1-6}$ alkyl; $R^7$ is halogen, cyano, $C_{3-5}$ cycloalkyl or $C_{1-6}$ haloalkyl; $R^5$ is hydrogen.

In a thirteenth embodiment of the present invention there is provided a compound according to formula III wherein $R^1$ is hydrogen or $C_{1-6}$ alkyl; $R^2$ is hydrogen, halogen, $C_{1-6}$ alkyl, $C_{1-6}$ alkoxy or $C_{3-5}$ cycloalkyl; and, $R^5$ is hydrogen, $CH_2OH$ or $CH_2OC(=O)(CH_2)_2C(=O)OH$; and, $R^7$ is halogen, cyano, $C_{3-5}$ cycloalkyl or $C_{1-6}$ haloalkyl; or, a pharmaceutically acceptable thereof.

In fourteenth embodiment of the present invention there is provided a compound according to formula III wherein $R^1$ is hydrogen or $C_{1-6}$ alkyl; $R^2$ is hydrogen, halogen, $C_{1-6}$ alkyl, $C_{1-6}$ alkoxy or $C_{3-5}$ cycloalkyl; and, $R^5$ is hydrogen; and, $R^7$ is halogen, cyano, $C_{3-5}$ cycloalkyl or $C_{1-6}$ haloalkyl; or, a pharmaceutically acceptable thereof.

In a fifteenth of the present invention there is provided a method for treating an HIV-1 infection, or preventing an HIV-1 infection, or treating AIDS or ARC, comprising administering to a host in need thereof a therapeutically effective amount of a compound according to formula I wherein $R^1$, $R^2$, $R^3$, $R^4$, $R^5$, X, Y, and Ar are as defined herein above; or a pharmaceutically acceptable salt thereof.

In sixteenth embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, $R^4$, $R^5$, X, Y, and Ar are as defined herein above and a therapeutically effective amount of at least one compound selected from the group consisting of HIV protease inhibitors, nucleoside reverse transcriptase inhibitors, non-nucleoside reverse transcriptase inhibitors, integrase inhibitors, CCR5 antagonists and viral fusion inhibitors.

In a seventeenth embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, $R^4$, $R^5$, X, Y, and Ar are as defined herein above and a therapeutically effective amount of at least one compound selected from the group consisting of zidovudine, lamivudine, didanosine, zalcitabine, stavudine, rescriptor, sustiva, viramune, efavirenz, etravirine, nevirapine, delavirdine, saquinavir, ritonavir, nelfmavir, indinavir, amprenavir, lopinavir or enfuvirtide, maraviroc or raltegravir.

In another embodiment of the present invention there is provided a method for treating an HIV-1 infection, or preventing an HIV-1 infection, or treating AIDS or ARC, comprising co-administering to a host in need thereof a therapeutically effective amount of a compound according to formula I wherein $R^1$, $R^2$, $R^3$, $R^4$, $R^5$, X, Y, and Ar are as defined herein above and a therapeutically effective amount of at least one compound selected from the group consisting of zidovudine, lamivudine, didanosine, zalcitabine, stavudine, rescriptor, sustiva, viramune, efavirenz, nevirapine, delavirdine, saquinavir, ritonavir, nelfinavir, indinavir, amprenavir, lopinavir or enfuvirtide.

In eighteenth embodiment of the present invention there is provided a method for inhibiting HIV reverse transcriptase in a host infected with HIV-1 comprising administering a therapeutically effective amount of a compound according to formula I wherein $R^1$, $R^2$, $R^3$, $R^4$, $R^5$, X, Y, and Ar are as defined herein above; or a pharmaceutically acceptable salt thereof.

In a nineteenth embodiment of the present invention there is provided a method for inhibiting HIV reverse transcriptase in a host infected with a strain of HIV-1 expressing a reverse transcriptase with at least one mutation compared to wild type HIV 1 said method comprising administering a therapeutically effective amount of a compound according to formula I wherein $R^1$, $R^2$, $R^3$, $R^4$, $R^5$, X, Y, and Ar are as defined herein above; or a pharmaceutically acceptable salt thereof.

In twentieth another embodiment of the present invention there is provided a method for inhibiting HIV reverse transcriptase in a host infected with a strain of HIV-1 expressing a reverse transcriptase with reduced susceptibility to efavirenz, nevirapine, delavirdine or etravirine compared to wild type reverse transcriptase said method comprising administering a therapeutically effective amount of a compound according to formula I wherein $R^1$, $R^2$, $R^3$, $R^4$, $R^5$, X, Y, and Ar are as defined herein above; or a pharmaceutically acceptable salt thereof.

In an embodiment of the present invention there is provided a method for treating an HIV-1 infection, or preventing an HIV-1 infection, or treating AIDS or ARC, comprising administering to a host in need thereof a therapeutically effective amount of a compound according to formula III wherein $R^1$ is hydrogen or $C_{1-6}$ alkyl; $R^2$ is hydrogen, halogen, $C_{1-6}$ alkyl, $C_{1-6}$ alkoxy or $C_{3-5}$ cycloalkyl; and, $R^3$ is hydrogen, $CH_2OH$ or $CH_2OC(=O)(CH_2)_2C(=O)OH$; and, $R^7$ is halogen, cyano, $C_{3-5}$ cycloalkyl or $C_{1-6}$ haloalkyl; or, a pharmaceutically acceptable thereof.

In a twenty-first embodiment of the present invention there is provided a pharmaceutical composition comprising a compound according to formula I wherein $R^1$, $R^2$, $R^3$, $R^4$, $R^5$, X, Y, and Ar are as defined herein above; or a pharmaceutically acceptable salt thereof and at least one pharmaceutically acceptable carrier, diluent or excipient. In an embodiment of the present invention there is provided a pharmaceutical composition comprising a compound according to formula III wherein $R^1$ is hydrogen or $C_{1-6}$ alkyl; $R^2$ is hydrogen, halogen, $C_{1-6}$ alkyl, $C_{1-6}$ alkoxy or $C_{3-5}$ cycloalkyl; and, $R^3$ is hydrogen, $CH_2OH$ or $CH_2OC(=O)(CH_2)_2C(=O)OH$; and, $R^7$ is halogen, cyano, $C_{3-5}$ cycloalkyl or $C_{1-6}$ haloalkyl; or, a pharmaceutically acceptable thereof and at least one pharmaceutically acceptable carrier, diluent or excipient. In another embodiment of the invention there is provided a compound selected from the compounds I-1 to I-21 of TABLE I.

The term "wild type" as used herein refers to the HIV virus strain that possesses the dominant genotype, which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA. Recent progress in development of RTI and PI inhibitors has been reviewed: F. M. Uckun and O. J. D'Cruz, *Exp. Opin. Ther. Pat.* 2006 16:265-293; L. Menendez-Arias, *Eur. Pharmacother.* 2006 94-96 and S. Rusconi and O. Vigano, *Future Drugs* 2006 3(1):79-88.

A-M. Vandamme et al. (*Antiviral Chemistry & Chemotherapy*, 1998 9:187-203) disclose current HAART clinical treatments of HIV-1 infections in man including at least triple drug combinations. Highly active anti-retroviral therapy (HAART) has traditionally consisted of combination therapy with nucleoside reverse transcriptase inhibitors (NRTI), non-nucleoside reverse transcriptase inhibitors (NNRTI) and protease inhibitors (PI). These compounds inhibit biochemical processes required for viral replication. While HAART has dramatically altered the prognosis for HIV infected persons, there remain many drawbacks to the current therapy including highly complex dosing regimes and side effects which can be very severe (A. Carr and D. A. Cooper, *Lancet* 2000 356(9239):1423-1430). Moreover, these multidrug therapies do not eliminate HIV-1 and long-term treatment usually results in multidrug resistance, thus limiting their utility in long-term therapy. Development of new therapeutics which can be used in combination with NRTIs, NNRTIs, PIs and viral fusion inhibitors to provide better HIV-1 treatment remains a priority.

Typical suitable NRTIs include zidovudine (AZT; RETROVIR®); didanosine (ddI; VIDEX®); zalcitabine (ddC; HIVID®); stavudine (d4T; ZERIT®); lamivudine (3TC; EPIVIR®); abacavir (ZIAGEN®); adefovir dipivoxil [bis(POM)-PMEA; PREVON®]; lobucavir (BMS-180194), a nucleoside reverse transcriptase inhibitor disclosed in EP-0358154 and EP-0736533; BCH-10652, a reverse transcriptase inhibitor (in the form of a racemic mixture of BCH-10618 and BCH-10619) under development by Biochem Pharma; emitricitabine [(−)-FTC] in development by Triangle Pharmaceuticals; β-L-FD4 (also called β-L-D4C and named β-L-2',3'-dicleoxy-5-fluoro-cytidene) licensed Vion Pharmaceuticals; DAPD, the purine nucleoside, (−)-β-D-2,6-diamino-purine dioxolane disclosed in EP-0656778 and licensed to Triangle Pharmaceuticals; and lodenosine (FddA), 9-(2,3-dideoxy-2-fluoro-β-D-threo-pentofuranosyl) adenine, an acid stable purine-based reverse transcriptase inhibitor under development by U.S. Bioscience Inc.

Four NNRTIs have been approved in the USA: nevirapine (BI-RG-587; VIRAMUNE®) available from Boehringer Ingelheim (B1'); delaviradine (BHAP, U-90152; RESCRIPTOR®) available from Pfizer; efavirenz (DMP-266, SUSTIVA®) a benzoxazin-2-one from BMS and etravirine (TMC-125; INTELENCE®) from Tibotec. Other NNRTIs currently under investigation include PNU-142721, a furopyridine-thio-pyrimide under development by Pfizer; capravirine (S-153 or AG-1549; 5-(3,5-dichlorophenyl)-thio-4-isopropyl-1-(4-pyridyl)methyl-1H-imidazol-2-ylmethyl carbonate) by Shionogi and Pfizer; emivirine [MKC-442; (1-(ethoxy-methyl)-5-(1-methylethyl)-6-(phenylmethyl)-(2, 4(1H,3H)-pyrimidinedione)] by Mitsubishi Chemical Co. and Triangle Pharmaceuticals; (+)-calanolide A (NSC-675451) and B, coumarin derivatives disclosed in NIH U.S. Pat. No. 5,489,697, licensed to Sarawak/Advanced Life Sciences; etravirine (TMC-125; 4-[6-amino-5-bromo-2-(4-cyano-phenylamino)-pyrimidin-4-yloxy]-3,5-dimethyl-benzonitrile) and DAPY (TMC120; 4-{4-[4-((E)-2-cyano-vinyl)-2,6-dimethyl-phenylamino]-pyrimidin-2-ylamino}-benzonitrile) by Tibotec-Virco and Johnson & Johnson; BILR-355 BS (12-ethyl-8-[2-(1-hydroxy-quinolin-4-yloxy)-ethyl]-5-methyl-11,12-dihydro-5H-1,5,10,12-tetraaza-dibenzo[a,e]cyclocten-6-one by Boehringer-Ingleheim; PHI-236 (7-bromo-3-[2-(2,5-dimethoxy-phenyl)-ethyl]-3,4-dihydro-1H-pyrido[1,2-a][1,3,5]triazine-2-thione) and PHI-443 (TMC-278, 1-(5-bromo-pyridin-2-yl)-3-(2-thiophen-2-yl-ethyl)-thiourea) by Paradigm Pharmaceuticals.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN® as well as nonpeptide protease inhibitors e.g., VIRACEPT®.

Typical suitable PIs include saquinavir available in hard gel capsules as INVIRASE® and in soft gel capsules as FORTOVASE® from Roche; ritonavir (ABT-538) available as NORVIR-from Abbott Laboratories; Lopinavir (ABT-378) also available from Abbot; KALETRA®, is co-formulation lopinavir and a sub-therapeutic dose of ritonavir available from Abbott Laboratories; indinavir (MK-639) available as CRIXIVAN® from Merck & Co.; nelfnavir (AG-1343) available as VIRACEPT® from Agouron Pharmaceuticals, Inc.; amprenavir (141W94) available as AGENERASE® from Vertex Pharmaceuticals, Inc. and GSK; tipranavir (PNU-140690) available as APTIVUS® from BI; lasinavir (BMS-234475/CGP-61755) by BMS; BMS-2322623, an azapeptide under development by BMS as a 2nd-generation HIV-1 PI; GW-640385X (VX-385) under development in a collaboration between GSK and Vertex; AG-001859 in preclinical development by Agouron/Pfizer; SM-309515 under development by Sumitomo Pharmaceuticals.

Additional PIs in preclinical development include N-cycloalkylglycines by BMS, α-hydroxyarylbutanamides by Enanta Pharmaceuticals; α-hydroxy-γ-[[(carbocyclic- or heterocyclic-substituted)amino)carbonyl]alkanamide derivatives; γ-hydroxy-2-(fluoroalkylaminocarbonyl)-1-piperazinepentanamides by Merck; dihydropyrone derivatives and α- and β-amino acid hydroxyethylamino sulfonamides by Pfizer; and N-amino acid substituted L-lysine derivatives by Procyon.

Entry of HIV into target cells requires CD-4 cell surface receptor and the CCR5 (M-tropic strains) and CXCR4 (T-tropic strains) chemokine co-receptors. Chemokine antagonize which block viral binding to the chemokines are useful inhibitors of viral infection. Takeda's identified TAK-779 as a potential CCR5 antagonist. (M. Shiraishi et al., *J.*

Med. Chem. 2000 43(10):2049-2063; M. Babba et al. *Proc. Nat. Acad. Sci. USA* 1999 96:5698-5703) and TAK-220 (C. Tremblay et al. *Antimicrob. Agents Chemother.* 2005 49(8): 3483-3485). WO0039125 (D. R. Armour et al.) and WO0190106 (M. Perros et al.) disclose heterocyclic compounds that are potent and selective CCR5 antagonists. Miraviroc (UK-427,857; MVC) has advanced by Pfizer to phase II clinical trials and show activity against HIV-1 isolates and laboratory strains (P. Dorr et al., *Antimicrob. Agents Chemother.* 2005 49(11):4721-4732; A. Wood and D. Armour, *Prog. Med. Chem.* 2005 43:239-271; C. Watson et al., *Mol. Pharm.* 2005 67(4):1268-1282; M. J. Macartney et al., 43rd *Intersci. Conf Antimicrob. Agents Chemother.* Sep. 14-17, 2003, Abstract H-875). Schering has advanced Sch-351125 (SCH-C) into Phase I/II clinical studies and reported the advance of a more potent follow-up compound, Vicroviroc (Sch-417690, SCH-D) into Phase I studies. (S. W. McCrombie et al., WO00066559; B. M. Baroudy et al. WO00066558; A. Palani et al., *J. Med. Chem.* 2001 44(21): 3339-3342; J. R. Tagat et al., *J. Med. Chem.* 2001 44(21): 3343-3346; J. A. Esté, *Cur. Opin. Invest. Drugs* 2002 3(3): 379-383; J. M. Struzki et al. *Proc. Nat. Acad. Sci. USA* 2001 98:12718-12723). Merck has disclosed the preparation of (2S)-2-(3-chlorophenyl)-1-N-(methyl)-N-(phenylsulfonyl) amino]-4-[spiro(2,3-dihydrobenzothiophene-3,4'-piperidin-1'-yl)butane S-oxide (1) and related derivatives with good affinity for the CCR5 receptor and potent-HIV activity. (P. E. Finke et al., *Bioorg. Med. Chem. Lett.,* 2001 11:265-270; P. E. Finke et al., *Bioorg. Med. Chem. Lett.,* 2001 11:2469-2475; P. E. Finke et al., *Bioorg. Med. Chem. Lett.,* 2001 11:2475-2479; J. J. Hale et al., *Bioorg. Med. Chem. Lett.,* 2001 11:2741-22745; D. Kim et al., *Bioorg. Med. Chem. Lett.,* 2001 11:3099-3102) C. L. Lynch et al. *Org. Lett.* 2003 5:2473-2475; R. S. Veazey et al. *J. Exp. Med.* 2003 198:1551-1562. GSK-873140 (ONO-4128, E-913, AK-602) was identified in a program initiated at Kumamoto University (K. Maeda et al. *J. Biol. Chem.* 2001 276:35194-35200; H. Nakata et al. *J. Virol.* 2005 79(4):2087-2096) and has been advanced to clinical trials. In WO00/166525; WO00/187839; WO02/076948; WO02/076948; WO02/079156, WO2002070749, WO2003080574, WO2003042178, WO2004056773, WO2004018425 Astra Zeneca disclose 4-amino piperidine compounds which are CCR5 antagonists. In U.S. Publication No. 20050176703 published Aug. 11, 2005, S. D. Gabriel and D. M. Rotstein disclosed heterocyclic CCR5 antagonist capable of preventing HIV cell entry. In U.S. Publication No. 20060014767 published Jan. 19, 2006, E. K. Lee et al. disclosed heterocyclic CCR5 antagonist capable of preventing HIV cell entry.

Attachment Inhibitors effectively block interaction between viral envelope proteins and chemokine receptors or CD40 protein. TNX-355 is a humanized IgG4 monoclonal antibody that binds to a conformational epitope on domain 2 of CD4. (L. C. Burkly et al., *J. Immunol.* 1992 149:1779-87) TNX-355 can inhibit viral attachment of CCR5-, CXCR4- and dual/mixed tropic HIV-1 strains. (E. Godofsky et al., *In Vitro* Activity of the Humanized Anti-CD4 Monoclonal Antibody, TNX-355, against CCR5, CXCR4, and Dual-Tropic Isolates and Synergy with Enfuvirtide, 45*th Annual Interscience Conference on Antimicrobial Agents and Chemotherapy (ICAAC)*. Dec. 16-19, 2005, Washington D.C. Abstract # 3844; D. Norris et al. TNX-355 in Combination with Optimized Background Regime (OBR) Exhibits Greater Antiviral Activity than OBR Alone in HIV-Treatment Experienced Patients, 45*th Annual Interscience Conference on Antimicrobial Agents and Chemotherapy (ICAAC)*. Dec. 16-19, 2005, Washington D.C. Abstract # 4020.)

Other antiviral agents include hydroxyurea, ribavirin, IL-2, IL-12, pentafuside. Hydroxyurea (Droxia), a ribonucleoside triphosphate reductase inhibitor shown to have a synergistic effect on the activity of didanosine and has been studied with stavudine. IL-2 (aldesleukin; PROLEUKIN®) is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314. Pentafuside (FUZEON®) a 36-amino acid synthetic peptide that inhibits fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Ribavirin, 1-β-D-ribofuranosyl-1H-1,2,4-triazole-3-carboxamide.

Commonly used abbreviations include: acetyl (Ac), aqueous (aq.), atmospheres (Atm), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), 1,5-diazabicyclo [4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DLAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-BuMe2Si (TBDMS), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), trimethylsilyl or $Me_3$ Si (TMS), p-toluenesulfonic acid monohydrate (TsOH or pTsOH), 4-Me—$CHSO_2$— or tosyl (Ts), N-urethane-N-carboxyanhydride (UNCA). Conventional nomenclature including the prefixes normal (n), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I

| CPD No. | STRUCTURE | mw | ms | mp |
|---|---|---|---|---|
| I-1 | 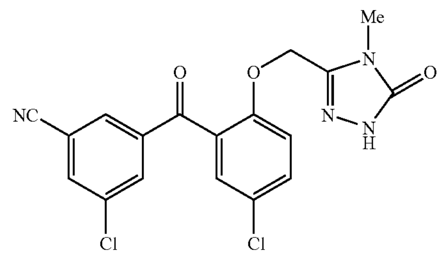 | 403.22 | | 210.0-213.9 |
| I-2 | formate salt | 409.2 | | 221.0-225.0 |
| I-3 | 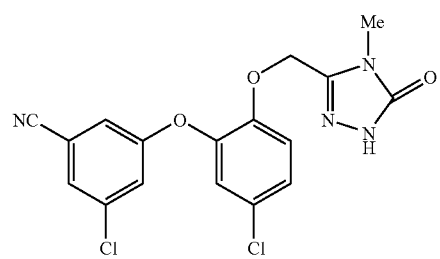 | 391.21 | 391 & 393 | 176-177 |
| I-4 | TFA salt | 469.22 | | 199.2-201.0 |
| I-5 | 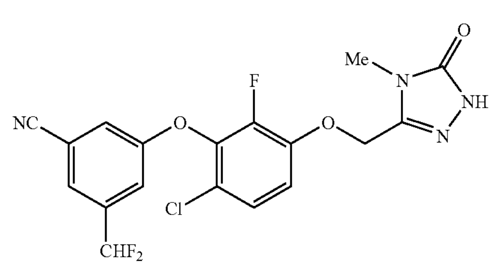 | 424.77 | | 184.5-185.3 |

TABLE I-continued

| CPD No. | STRUCTURE | mw | ms | mp |
|---|---|---|---|---|
| I-6 | 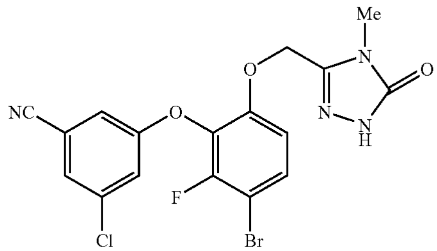 | 453.65 | | 192.5-193.0 |
| I-7 | 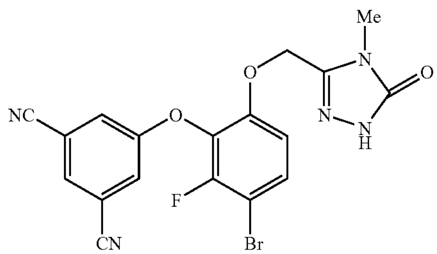 | 444.22 | | 205.5-207.0 |
| I-8 | 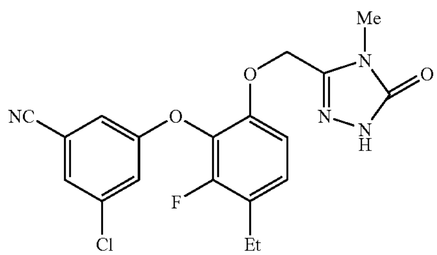 | 402.81 | 403 | |
| I-9 | 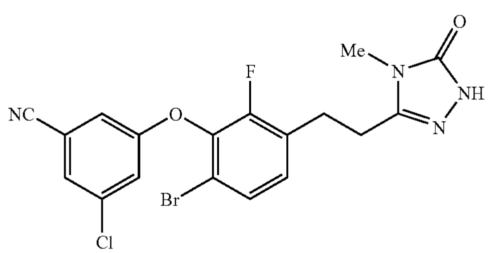 | 451.68 | 451 & 453 | 186.0-187.0 |
| I-10 | 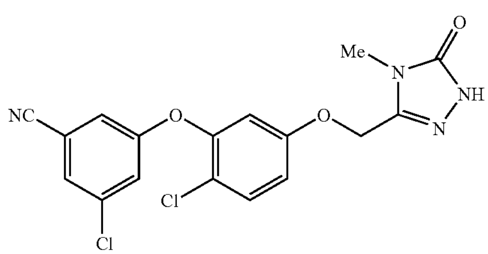 | 391.21 | | 80.0-81.0 |
| I-11 | 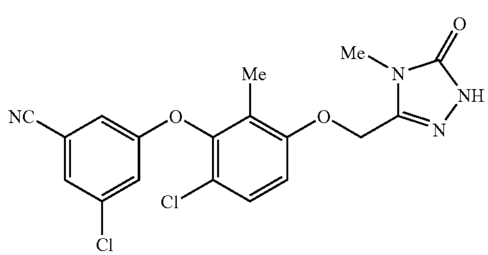 | 405.24 | | 196-198 |

TABLE I-continued

| CPD No. | STRUCTURE | mw | ms | mp |
|---|---|---|---|---|
| I-12 | 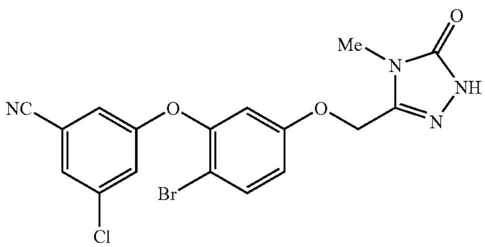 | 435.66 | 435 & 437 M+ | 95.2-100.7 |
| I-13 | 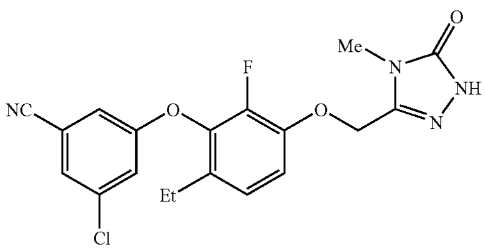 | 402.81 | 403 & 405 | 179.0-180.0 |
| I-14 | 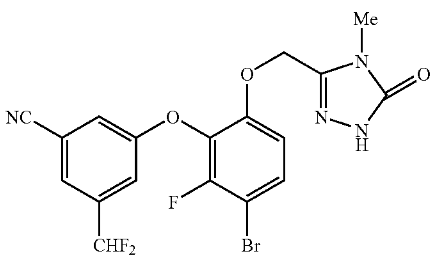 | 569.22 | | 193.0-194.0 |
| I-15 | 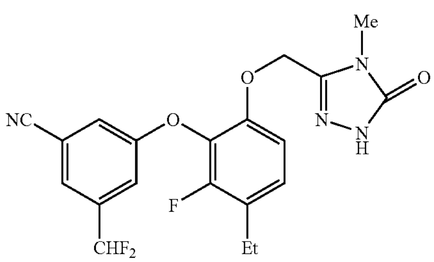 | 418.37 | | 160.0-161.0 |
| I-16 | 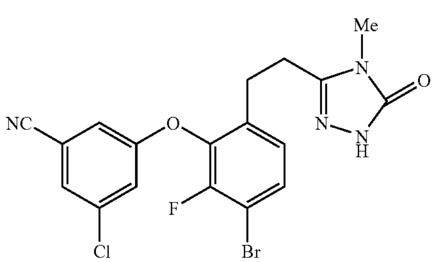 | 451.68 | | 212.4-214.2 |
| I-17 | 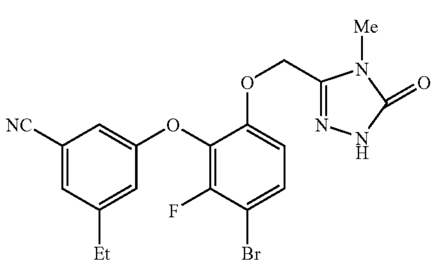 | 447.26 | | 207.0-208.0 |

TABLE I-continued

| CPD No. | STRUCTURE | mw | ms | mp |
|---|---|---|---|---|
| I-18 | [structure] | 396.42 | | 164.0-166.0 |
| I-19 | [structure] | 408.43 | | 166.0-168.0 |
| I-20 | [structure] | 501.23 | | 197.1-202.1 |
| I-21 | [structure] | 425.66 | | 224.4-225.6 |

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, $2^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted with generalized Markush structures; however, one skilled in the art will immediately appreciate that the nature and number of the R groups do not alter the applicability of the synthetic procedures. The general formulae and reaction sequences in the schemes are intended to be illustrative and are not intended to imply a limitation to the scope of the invention which is defined by the appended claims. Moreover, the reaction conditions are exemplary and alternative conditions are well known. The reaction sequences in the following examples are not meant to limit the scope of the invention as set forth in the claims.

Compounds of the present invention in which the pendant triazolone chain wherein Y is O is meta to an aryloxy moiety (SCHEME A) are prepared from a 4-nitro-3-aryloxyphenol (A-5) which can prepared from 2,3,4-trifluoronitrobenzene or 2,4-dinitrobenzene by a two step process comprising nucleophilic aromatic displacement of the 2-fluoro by an appropriately substituted phenol and subsequent displacement of the 4-fluoro with benzaldehyde oxime under conditions which result in cleavage of the N—O bond (R. D. Knudsen and H. R. Snyder, *J. Org. Chem.* 1974 39(23):3343-3346). One skilled in the art will appreciate that the reaction can carried out with a variety of phenols allowing diverse substituents and substitution patterns on the aryl ring.

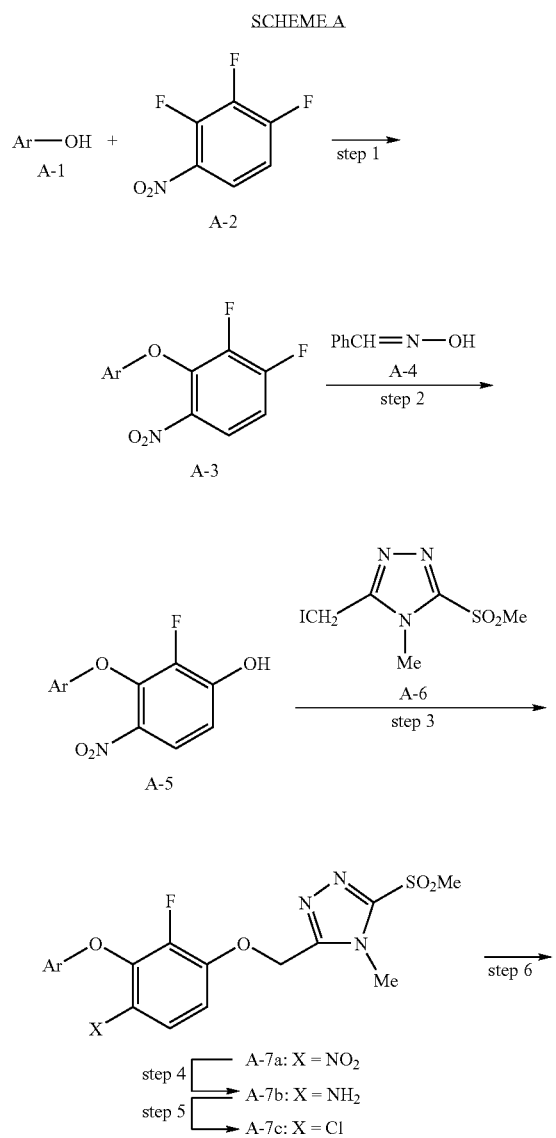

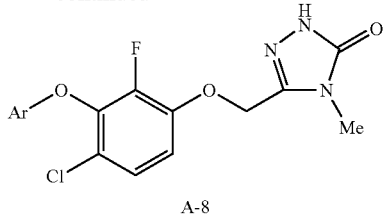

Fluoronitroaromatic compounds are known to be unusually sensitive to nucleophilic attack by soft nucleophiles. Fluorine substituents are generally significantly more labile than other halogen substituents. While hard nucleophiles like water and hydroxide fail to displace fluoride, soft nucleophiles like phenols, imidazoles, amines, thiols and some amides undergo facile displacement reactions even at room temperature (D. Boger et al., *Biorg. Med. Chem. Lett.* 2000 10: 1471-75; F. Terrier *Nucleophilic Aromatic Displacement: The Influence of the Nitro Group* VCH Publishers, New York, N.Y. 1991). In U.S. Pat. No. 5,292,967 issued Mar. 8, 1994 T. Papenfuhs et al. disclose a process for preparing 2,3-difluoro-6-nitro-phenol in good yields and high selectivity by treating A-2 with an alkali metal hydroxide and an alkaline metal hydroxide. J. H. Marriott et al. (*J. Chem. Soc. Perkin I* 2000 4265-4278) disclose the addition of alkali alkoxides to preponderantly to the para position of pentafluoro-nitro-benzene under phase-transfer conditions (DCM/aq NaOH/Bu$_4$N$^+$ HSO$_4^-$/RT). 2,4-difluoro-nitro-benzene reacted non-regioselectively to afford both para and ortho displacement. The reaction of sodium methoxide with 2,3,4-trifluoronitrobenzene in methanol has been reported to afford an inseparable mixture of the corresponding 2- and 4-monomethoxy and 2,4-dimethoxy derivatives (P. M. O'Neill et al., *J. Med. Chem.* 1994 37:1362-70). Displacement of the ortho-fluorine of 2,4-difluoro-nitrobenzene by amine nucleophiles also has been reported. (W. C. Lumma, Jr. et al., *J. Med. Chem.* 1981 24:93-101).

Introduction of the 4-methyl-2,4-dihydro-[1,2,4]triazol-3-one moiety is accomplished by O-alkylation of A-5 with 3-iodomethyl-5-methanesulfonyl-4-methyl-4H-[1,2,4]triazole which is prepared as depicted in SCHEME B. Condensation of ethyl hydroxy acetate and 4-methyl-3-thiosemicarbazide afforded 5-ethyl-4-methyl-2,4-dihydro-[1,2,4]triazole-3-thione (B-3) which is S-alkylated (step 2), converted to the chloromethyl compound (step 3), oxidized to the sulfone (step 4) and converted to the desired iodomethyl compound B-5b via a Finkelstein reaction (step 5).

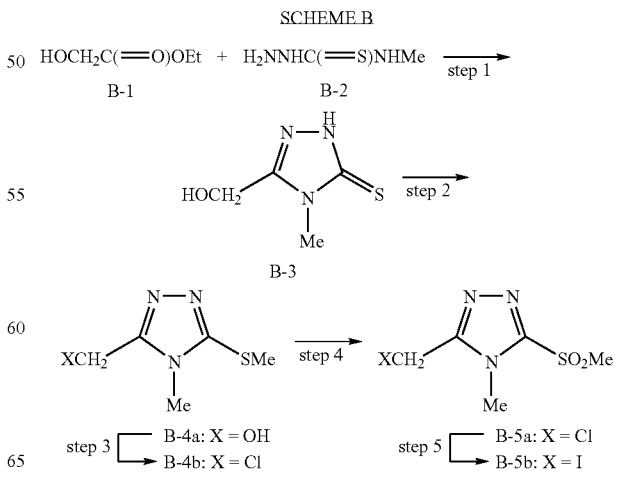

The nitro substituent in A-7a can be readily converted to other functional groups by reduction to the corresponding amine which can be diazotized and subsequently displaced by a variety of nucleophiles. Reduction of the nitro group can be carried out with a variety of well-known reducing agents. For example an activated metal such as activated iron, zinc or tin (produced for example by washing iron powder with a dilute acid solution such as dilute hydrochloric acid). The reduction can also be carried out under a hydrogen atmosphere in the presence of an inert solvent in the presence of a metal effective to catalyze hydrogenation reactions such as platinum or palladium. Other reagents which have been used to reduce nitro compounds to amines include $AlH_3$—$AlCl_3$, hydrazine and a catalyst, $TiCl_3$, Al—$NiCl_2$-THF, formic acid and Pd/C and sulfides such as NaHS, $(NH_4)_2S$ or polysulfides (i.e. the Zinn reaction). Aromatic nitro groups have been reduces with $NaBH_4$ or $BH_3$ in the presence of catalysts such as $NiCl_2$ and $CoCl_2$. Thus for example, reduction may be effected by heating the nitro group in the presence of a sufficiently activated metal such as Fe and a solvent or diluent such as $H_2O$ and alcohol, for example MeOH or EtOH at a temperature in the range of 50 to 150° C., conveniently at about 70° C. (J. March, *Advanced Organic Chemistry*, John Wiley & Sons: New York, N.Y., 1992, p 1216)

Conversion of the aryl amine to an aryl halide was carried out by diazotization of the amine and displacement of the resulting diazonium group with a halide were carried using standard Sandmeyer conditions. Diazotization of the aryl amines is accomplished by treating the amine with nitrous acid which is commonly formed by treating an solution of the amine in dilute HCl with an aqueous solution of sodium nitrite at 0-10° C. Other mineral acids such as sulfuric acid and phosphoric acid can be used if the chloride counterion is undesirable. Diazotization of amines can be carried out in organic solvents such as HOAc, MeOH, EtOH, formamide and DMF in the presence of nitrous acid esters such as. butyl nitrite and pentyl nitrite. (K. Schank, Preparation of diazonium groups, In *The chemistry of diazonium and diazo groups, Part 2*; S. Patai, Ed.; John Wiley & Sons: New York, N.Y., 1978, p. 647-648) Conversion of the resulting diazonium salt to a chlorine or bromine is carried out in HCl/Cu(I)Cl or HBr/Cu(I)Br, respectively. Aryl bromide and chlorides can also be prepared from primary aromatic amines by treating the amine with tert-butyl nitrite and anhydrous $CuCl_2$ or $CuBr_2$ at 65° C. or with tert-butyl thionitrite or tert-butylthionitrate and $CuCl_2$ or $CuBr_2$ at RT. (J. March, *Advanced Organic Chemistry*, John Wiley & Sons: New York, N.Y., 1992, p 723)

Other compounds of the present invention are substituted with an alkyl or cycloalkyl group at the 4-position of the phenoxyacetic acid. Alkyl and alkenyl groups can be introduced utilizing the Negishi coupling of organozinc halides, dialkylzinc or dialkenyl zinc with haloarenes and aryl triflates is an effective means for attachment of an alkyl group to an arene (E.-I. Negishi, *Acc. Chem. Res.* 1982 15:340-348). The reaction is catalyzed by palladium Pd(0) and palladium is preferably ligated to a bidentate ligand including Pd(dppf)$Cl_2$ and Pd(dppe)$Cl_2$. (J. M. Herbert *Tetrahedron Lett.* 2004 45:817-819) Typically the reaction is run an inert aprotic solvent and common ethereal solvents include dioxane, DME and THF are suitable. The reaction is commonly run at elevated temperature. The Negishi reaction was utilized to introduce methyl and ethyl substituents.

The 4-cyclopropyl substituent is introduced in two steps by palladium-catalyzed coupling ethenyltrimethyltin mediated displacement the aryl bromide (the Stille Reaction) and cyclopropanation of the resulting olefin. The cyclopropanation was achieved Pd(OAc)$_2$ catalyzed cycloaddition of diazomethane. Other cyclopropanation conditions are well known in the art and could be adapted to this substrate.

The Stille cross-coupling reaction is a palladium-catalyzed coupling of an aryl or vinyl stannanes with aryl or vinyl halides or -sulfonyloxy compounds (J. K. Stille, *Angew. Chem. Int. Ed.* 1986 25:508-524; A. F. Littke and G. C. Fu, *Angew. Chem. Int. Ed.* 1999, 38:2411-2413). Commercially available Pd reagents including Pd(PPh$_3$)$_4$, Pd(OAc)$_2$ and Pd$_2$(dba)$_3$ can be used. Phosphine ligands are useful rate accelerants if they are not a component of the palladium catalyst. Relatively poorly electron-donating ligands tend to provide the greatest rate acceleration (V. Farina and B. Krishnan, *J. Am. Chem. Soc.* 1991 113:9585-9595). Additives including CuI have been incorporated to provide rate accelerations (V. Farina et al., *J. Org. Chem.* 1994 59:5905-5911). The reaction is typically run in aprotic solvents at elevated temperature.

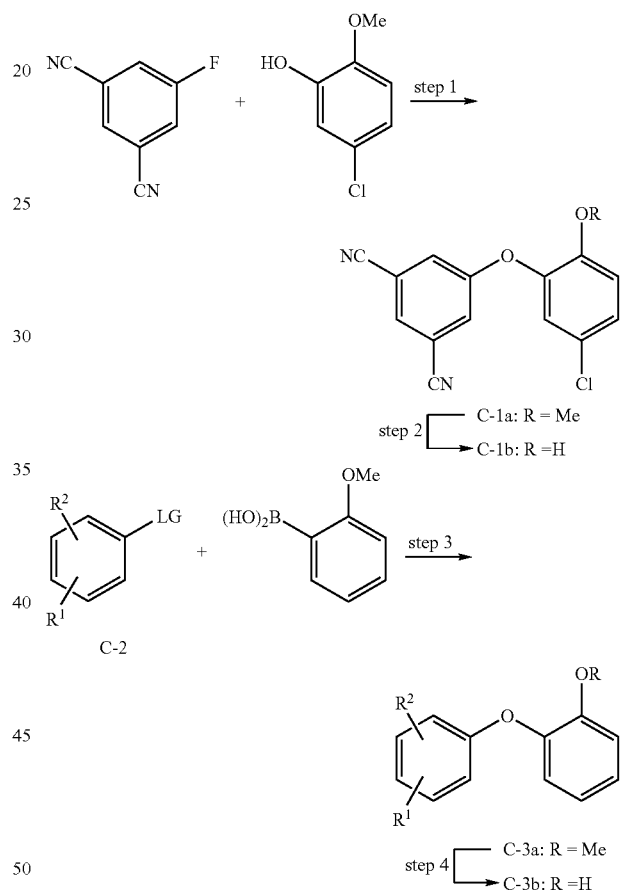

SCHEME C

2-Aryloxy-phenols are precursors to compounds of the present invention in which the pendant triazolone chain is ortho to aryloxy moiety. 2-Aryloxy-phenols can be prepared by methodology known in the art. The preparation of diaryl ethers has been reviewed (J. S. Sawyer, Recent Advances in Diaryl Ether Synthesis, *Tetrahedron* 2000 56:5045-5065). Introduction of the aryloxy ether can often be accomplished by direct $S_NAR$ displacement reaction on a aromatic ring substituted with a leaving group and electron withdrawing group, e.g. 3-fluoro-iso-phthalonitrile [CASRN 453565-554] by guiacol and demethylation of the resulting phenol. Other aryl fluorides also useful for compounds of the present invention include, but are not limited to, 3-chloro-5-fluoro-benzonitrile [CASRN 327056-73-5], 3-difluoromethyl-3-fluoro-benzonitrile [CASRN 867366-77-6] and 3,5-difluoro-benzonitrile [CASRN 64248-63-1]. (L. H. Jones and C. Mowbray, *Syn. Lett.* 2006, 9:1404-1406)

Aryl ethers also can be efficiently prepared by Cu(OAc)$_2$ catalyzed condensation of substituted benzene boronic acids and phenols (D. A. Evans et al., *Tetrahedron Lett.* 1998 39:2937-2940 and D. M. T. Chan et al., *Tetrahedron Lett.* 1998 39:2933-2936). Benzene boronic acids with a variety of other substituents are widely available. Alternatively, variations of the Ullmann diaryl ether synthesis catalyzed by Cu(I) salts (J.-F. Marcoux et al., *J. Am. Chem. Soc.* 1997 119:10539-540; E. Buck et al., *Org. Lett.* 2002 4(9):1623-1626) or palladium-catalyzed coupling procedures also has been reported (G. Mann et al., *J. Am. Chem. Soc.* 1999 121:3224-3225) have been described. These protocols do not require strongly electronegative substituents to activate an aryl fluoride for SNAR displacements. One skilled in the art will appreciate that optimal procedure will vary depending on the nature and position of substituents on the aryl rings to be coupled and useful conditions for the coupling can by identified without undue experimentation.

SCHEME D

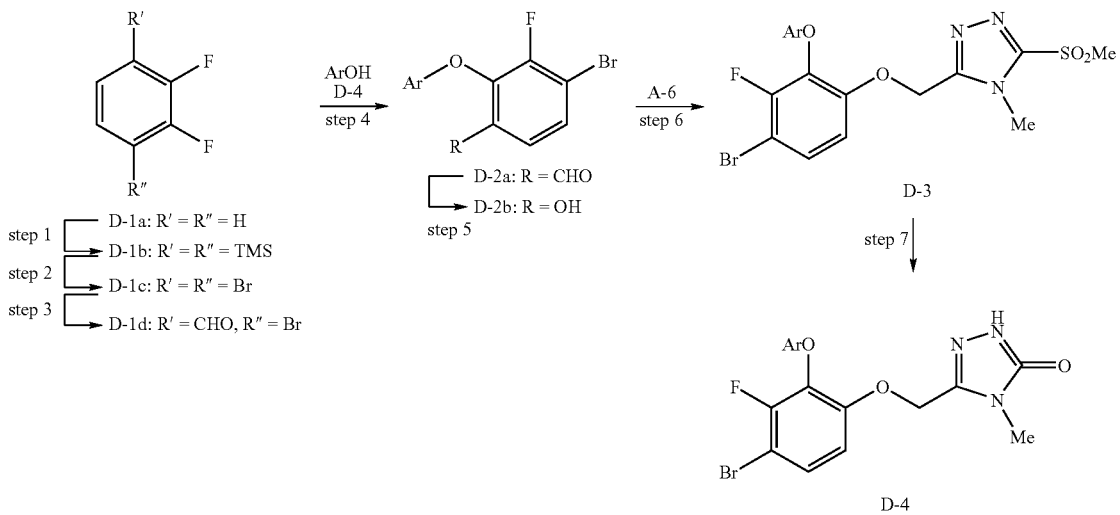

An alternate route leading to compounds of the present invention in which the pendant triazolone chain is ortho to aryloxy moiety utilizes the ortho fluoro benzaldehyde derivative D-1d which was treated with a suitable substituted phenol resulting in displacement of the fluorine ortho to formyl substituent. Baeyer-Villager oxidation and subsequent hydrolysis of the resulting formate ester converted the formyl group in D-2a to a phenol D-2b which can be elaborated A-6 as depicted in SCHEME A. Other useful starting materials which undergo analogous transformation to produce compounds of the present invention include 2,4-difluoro-3-methyl-nitrobenzene [CASRN 79562-49-5] and 3-chloro-2,4-difluoro-nitrobenzene [CASRN 3847-58-3]

SCHEME E

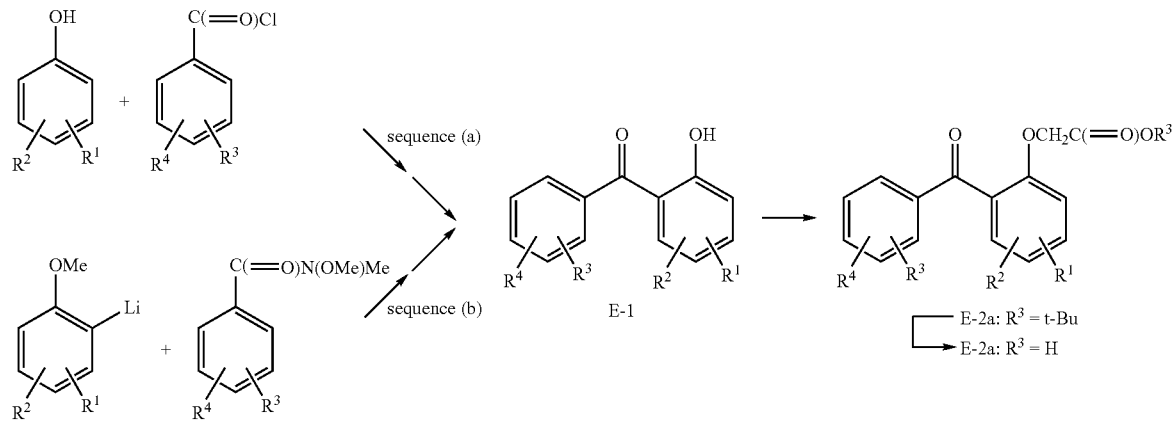

The preparation of 2-aroyl-phenol intermediates by acylation of a substituted phenol with an substituted aroyl chloride followed by a Fries rearrangement (sequence a) or by ortho-metallation of an anisole derivative and condensation with a suitably substituted N,O-dimethyl-N-hydroxy-benzamide (sequence b) as depicted in SCHEME E. (P. G. Wyatt et al., *J. Med. Chem.* 1995 38(10):1657-1665; J. H. Chan et al., *J. Med. Chem.* 2004 47(5):1175-1182; K. Romines et al., *J. Med. Chem.* 2006 49(2):727-739; C. W. Andrews et al. WO01/017982 published Mar. 15, 2002; and J. H. Chan et al. WO02/070470, published Sep. 12, 2002) These references are hereby incorporated by reference in their entirety.

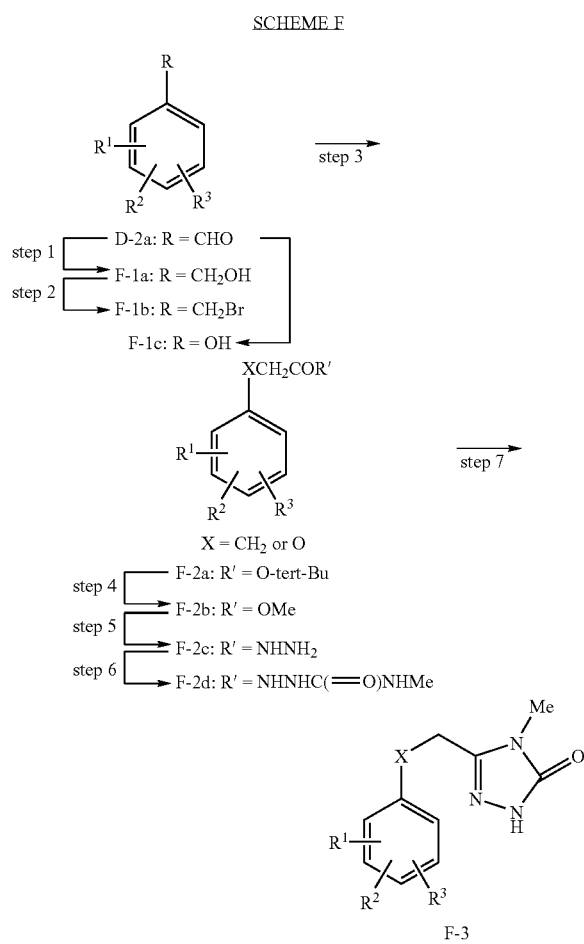

Introduction of the 4-methyl-2,4-dihydro-[1,2,4]triazol-3-one moiety onto C-3b, D-2b, or E-1 is accomplished by O-alkylation of F-1c with 3-iodomethyl-5-methanesulfonyl-4-methyl-4H-[1,2,4]triazole followed by hydrolysis of the methyl sulfone as depicted in SCHEME A. A suitably substituted phenol, F-1c, can also be alkylated with tert-butyl bromoacetate to afford F-2a which can be converted to a triazolone as disclosed by P. Dunn et al. in U.S. Patent Pub. 2004/0192704 published Sep. 30, 2004 which is incorporated by reference herein in its entirety (SCHEME F, steps 4-7).

The preparation of triazolones with a two-carbon linker (X=Y=CH$_2$) are readily accessible by elaboration of the triazolone ring onto a suitable substituted 2-aryl-propionic acid which can be prepared by homologation of an intermediate such as the benzaldehyde D-2a. Reduction of D-2a to the corresponding alcohol and bromide displacement affords F-1b which can be alkylated by tert-butyl acetate to afford F-2a (X=CH$_2$). One skilled in the art will appreciate that alternate reaction sequences are know to convert D-2a to F-2b (e.g., Horner-Emmons-Wadsworth homologation with ethyl (triphenyl-λ$^5$-phosphanylidene)-acetate and subsequent reduction of the olefin) or to convert F-1a to F-2b (e.g., alkylation with tert-butyl methyl malonate following by hydrolysis and decarboxylation.

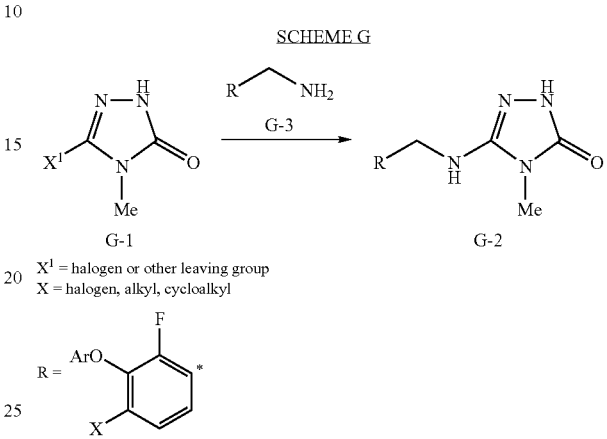

Substituted benzylamino-4-methyl-2,4-dihydro-[1,2,4]triazol-3-one derivatives G-2 can be prepared by condensation a 4-methyl-2,4-dihydro-[1,2,4]triazol-3-one derivative (G-1) containing a leaving group at the 5-position. For example, 5-bromo-4-methyl-2,4-dihydro-[1,2,4]triazol-3-one [CASRN 22354-80-9] could be treated with an amine G-3 in the presence of a catalytic palladium species. Introduction of primary or secondary amines by replacement of a leaving group on a (hetero)aryl ring can be accomplished by Buchwald-Hartwig palladium-catalyzed cross-coupling procedure (J. P. Wolfe and S. L. Buchwald *J. Org. Chem.* 2000 65:1144-1157 and *Acc. Chem. Res.* 1998 31:805-818; J. P. Wolfe et al. *J. Org. Chem.* 2000 65:1158; J. F. Hartwig, *Angew. Chem. Int. Ed.* 1998 37:2046-2067). Typical conditions include Pd(dppf)Cl$_2$ in the presence of base, e.g. sodium tert-butoxide or Cs$_2$CO$_3$, and aprotic solvent. Typical leaving groups include halogen and triflates and optimum leaving groups will depend on the precise reactant.

N-acyloxymethyl derivatives, I (R$^5$=CH$_2$OC(=O)(CH$_2$)$_n$C(=O)OH) wherein n is 2 to 5 can be prepared by exposing the triazolone to formaldehyde and acylating the resulting hydroxymethyl derivative as described by J. P. Dunn et al. in U.S. Patent Pub. 2006/0025462 published Feb. 2, 2006 which is incorporated herein by reference in its entirety.

Dosage and Administration

The compounds of the present invention may be formulated in a wide variety of oral administration dosage forms and carriers. Oral administration can be in the form of tablets, coated tablets, dragees, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" the substance is useful in preparing a pharmaceutical composition that is generally safe, non-toxic, and neither biologically nor otherwise undesirable and includes that which is acceptable for human pharmaceutical use. A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

REFERENCE EXAMPLE 1

3-Iodomethyl-5-methanesulfonyl-4-methyl-4H-[1,2,4]triazole (B-5b—SCHEME B)

step 1—Ethyl hydroxyacetate (99.8 g; 1.05 eq., 95%) and 4-methyl-3-thiosemicarbazide (96.0 g; 1.00 eq., 97%) were combined in a 2L-reactor equipped with a stirrer and reflux condenser. The reaction was stirred and heated under reflux overnight (the internal temperature drops from ca. 130° C. to 4-methyl-3-thiosemicarbazide 90° C. over this period). The reactor was configured for distillation and the distillation was continued until the internal temperature reached 130° C., then maintained under reflux until it dropped to ca. 100° C. Again, the reactor was configured for distillation, heated to 130° C. while distilling, then configured for reflux for 1 h. Finally, the reactor was again configured for distillation, 600 mL water was added, and distillation carried out while continually replacing distillate with water to drive off remaining ethanol. The solution was cooled to 60° C., where crystallization of the product began. The slurry was cooled to 5° C., filtered ("C"-grade filter frit), and washed once with water. Vacuum drying at 60° C. afforded 92.7 g (70%) of B-3.

steps 2 & 3—A solution of B-3 (92.0 g) methyl toluenesulfonate (129.7 g, 1.1 equivalent) and MeOH (1 L) in a 2L reactor was heated under reflux for 15 h. The MeOH was completely removed by distillation while continually replacing distillate with DCE. To the resulting DCE solution was added thionyl chloride (48.5 mL, 1.05 eq.) was added in one batch, then 72.5 g TEA (1.13 eq.) was added while stirring over 2 min. The temperature rose to 50° C. When the solution had cooled to 29° C., crystals began to form. Aqueous satd. $Na_2CO_3$ (1.1L) solution was combined with $H_2O$ (200 mL) and added to the mixture over 15 min. The organic phase was separated and washed with sat'd. $Na_2CO_3$ (100 mL). The original aqueous solution was extracted with DCE (500 mL) and this extract was then washed with sat'd. $Na_2CO_3$ (100 mL). The organic phases were combined, treated with activated charcoal (15 g) and filtered. The filtrate was concentrated to ⅓ of its volume by vacuum distillation, then toluene was continuously added to replace distilled solvent until the internal temperature reached 43° C., at which point the product began to crystallize out of solution. Distillation was stopped and the slurry was cooled to 6° C. and filtered ("C"-grade filter). The filter cake was washed once with only enough ice-cold toluene to completely wet the cake. The cake was dried to afford 69.6 g (61.9% over two steps)of B-4.

step 4—A solution of B-4 (69.5 g) and $HCO_2H$ (100 mL) was heated to 45° C. To the solution was added in one batch refrigerated 30% aq. $H_2O_2$ solution (89.3 g). A bath of room temperature water was used to maintain the reaction solution between 50-60° C. for 25 min. Another 95 g of refrigerated 30% aq. $H_2O_2$ solution was added in one batch and the flask was fitted with a heating mantle and maintained at 55-65° C. for 1 h while removing the mantle when necessary. To the resulting solution was added water (510 mL) over several minutes resulting in crystallization of the reaction product beginning at 49° C. and cooling to 33° C. The slurry was cooled to 10° C., filtered ("C"-grade filter) and washed with enough water to remove residual $H_2O_2$ (NaI test of filtrate). The cake was dried at 50° C. to afford 65.4 g (79.7%) of B-5a.

step 5—A mixture of B-5a (65.3 g), NaI (56.0 g, 1.2 equiv.) was dissolved in 450 mL acetone with stirring. The temperature rose to 32° C. and then subsided. After 2 h at ca. 22° C., the reaction was sufficiently complete. The reaction slurry was filtered ("M"-grade filter) and the cake washed twice with acetone. The filter flask was changed and the acetone filtrate saved. The cake was then washed with water (200 mL) and collected. The aqueous filtrate was discarded, the resulting cake and previous acetone filtrate were combined and resulting slurry was heated to distill the acetone while replacing the distillate with water. When the temperature reached 84° C., the heating was stopped and the solution cooled resulting in the crystallization of the reaction product. The slurry was filtered at RT, the cake was washed with water and dried at 60° C. to afford (76.4 g, 81.4%) of B-5b.

REFERENTIAL EXAMPLE 2

Phenols

Preparation of 3-chloro-5-hydroxy-benzonitrile (CASRN 473923-97-6)

step 1—A 100 ml round bottom flask was charged under a stream of nitrogen with 3,5-dichlorobenzonitrile (R-3a, 7.0 g, 40.69 mmol) and anhydrous DMF (75 mL). To the solution was added sodium methoxide (2.26 g, 44.76 mmol) and resulting solution was stirred further at RT for 24 h. When the reaction was complete, aqueous 10% HCl added dropwise to the reaction vessel. The crude mixture was extracted with EtOAc and sequentially washed with aqueous acid, water and brine. The EtOAc extracts were dried ($Na_2SO_4$), filtered and the solvent was removed in vacuo to afford a crude solid which was recrystallized from hexane/acetone to afford 5.9 g (86%) of 5-chloro-3-methoxy-benzonitrile.

step 2—A 250 mL flask was charged with 5-chloro-3-methoxy-benzonitrile (7.0 g, 41.766 mmol) and 2,4,6-collidine (100 mL). The mixture was heated to 170° C. and LiI (16.76 g, 125.298 mmol) was added and the reaction mixture was heated for 4 h. When R-3b was consumed the reaction was cooled to RT and quenched with 10% aqueous HCl. The resulting mixture was extracted with EtOAc and washed with water and brine. The EtOAc extract was dried over ($Na_2SO_4$) and filtered. The solvent was removed in vacuo to afford a yellow oil which was purified by silica gel chromatography eluting with EtOAc/hexane (10:90) to afford 6.0 g (94%) of 3-chloro-5-hydroxy-benzonitrile.

Preparation of 5-hydroxy-isophthalonitrile [CASRN 79370-78-8]

5-Hydroxy-isophthalonitrile was prepared as described by C. E. Mowbary et al., WO2004024147 published Mar. 25, 2004 in procedures 1-3.

3-cyano-5-difluoromethyl-phenol [CARN 874974-85-3]

step 1—A solution of 1,3-dibromo-5-fluoro-benzene (CASRN 1435-51-4), MeONa (1 equivalent) and DMF were stirred overnight under an $N_2$ atmosphere at RT. The volatile solvents were removed in vacuo and the residue partitioned between $Et_2O$ and water. The organic phase was washed with 5% NaOH, water and brine, dried ($MgSO_4$), filtered and evaporated to afford 1,3-dibromo-5-methoxy-benzene.

step 2—To a solution of 1,3-dibromo-5-methoxy-benzene (60 g, 0.2256 mol) and anhydrous $Et_2O$ (1 L) cooled to −78° C. and maintained under an Ar atmosphere was added dropwise over 30 min n-BuLi (100 mL, 0.2482 mol, 2.5M in hexane). The yellow solution was stirred at −78° C. for 20 min. To the reaction mixture was added dropwise dry DMF (19 mL, 248.2 mmol) over 15 min and the reaction stirred at −78° C. for 10 min before the cooling bath was removed and the reaction allowed to warm to −30° C. over 30 min. The reaction vessel was placed in an ice-water bath and warmed to −10° C. The mixture was slowly added to an ice cold saturated aqueous $NH_4Cl$ solution (400 mL). The organic layer was separated and the aqueous phase thrice extracted with $Et_2O$. The combined extracts were washed with water, dried ($MgSO_4$), filtered and evaporated to afford an oil which solidified on standing. The crude product was purified by $SiO_2$ chromatography eluting with a hexane/EtOAc gradient (3 to 5% EtOAc) to afford 3-bromo-5-methoxy-benzaldehyde.

step 3—A solution of 3-bromo-5-methoxy-benzaldehyde (1 mmol) in DMF (2 mL) is added to a round bottomed flask containing $Zn(CN)_2$ (0.7 equivalents), $Pd(PPh_3)_4(0)$ (0.2 equivalents) in DMF (15 mL). The reaction is stirred at 90° C. under an atmosphere of argon for 48 h. The reaction mixture is cooled and evaporated to dryness. The crude residue is dissolved in EtOAc, washed with brine solution, dried (MgSO$_4$) and evaporated. The crude product is purified by SiO$_2$ chromatography to afford 3-formyl-5-methoxy-benzonitrile.

step 4—DAST (21.04 mL, 519 mmol) was added to a solution of 3-formyl-5-methoxy-benzonitrile (15.1 g, 94 mmol) and DCM (100 mL) contained in a NALGENE® bottle under nitrogen. EtOH (0.013 mL, 0.23 mmol) was added, and the mixture was stirred for 16 h. The reaction mixture was then added slowly to an aqueous solution of saturated NaHCO$_3$. After the bubbling was ceased, DCM (50 mL) was added and the layers were separated. The organic layer was washed with brine (30 mL) and dried (MgSO$_4$). The solvent was removed and the crude product was purified by two flash SiO$_2$ chromatographies eluting with an EtOAc/hexanes gradient (0% to 10% EtOAc) to 3-difluoromethyl-5-methoxy-benzonitrile as a white solid.

step 5—3-Difluoromethyl-5-methoxy-benzonitrile was demethylated in a solution of 48% aqueous HBr and glacial HOAc heated to 120° C. until demethylation was complete. Removal of volatile solvents and partitioning between water and DCM afforded 3-difluoromethyl-5-hydroxy-benzonitrile.

Preparation of 3-bromo-5-cyano-phenol (CASRN 770718-92-8)

step 1—n-BuLi (2.6 mL of a 1.6 M solution, 1.1 equiv) was added slowly to a solution of the 1,3-dibromo-5-methoxy-benzene (1.0 g, 3.8 mmol, CAS Reg. No. 74137-36-3) in Et$_2$O (20 mL) cooled to −78° C. under an N$_2$ atmosphere. The solution was stirred for 45 min, and DMF was added via syringe. The solution was warmed slowly to RT, added to saturated ammonium chloride, and extracted with ether. The organic phase was washed with brine and dried (MgSO$_4$), filtered and evaporated to afford 0.80 g (98%) of 1-bromo-3-formyl-benzaldehyde.

step 2—A solution of 1-bromo-3-formyl-benzaldehyde (12.0 g, 56 mmol), hydroxylamine hydrochloride (19.4 g, 5 equiv), EtOH (100 mL) and pyridine (10 mL) was heated to 65° C. for 16 h. The mixture was cooled to RT, and partitioned between 50% EtOAc/hexanes and water. The organic layer was washed with brine and dried (MgSO$_4$). The volatile materials were evaporated to afford 12.4 g (97%) of the oxime. This material was dissolved in anhydrous dioxane (100 mL) and pyridine (26 mL, 6 equiv). The solution was cooled to 0° C., TFAA (15 mL, 2 equiv) was added, and the mixture was allowed to warm to RT. The solution was stirred for 2 d, and warmed to 60 C for 1 h. The mixture was cooled to RT, and added carefully to ice water. The mixture was extracted with DCM, and the combined organic layers were washed with water, 1 M HCl, and brine. The organic layer was dried (MgSO$_4$) and evaporated to afford 10.4 g (90%) of 3-bromo-5-methoxy-benzonitrile.

step 3—Anhydrous collidine (100 mL) was added to a dry flask containing 3-bromo-5-methoxy-benzonitrile (10.4 g, 49 mmol) and LiI (19.6 g, 3 equiv). The solution was heated under nitrogen to 150° C. overnight, cooled to RT, and poured into an ice cold 1 M HCl solution. The mixture was extracted with a 1:1 EtOAc/hexanes solution, washed with water, and dried (MgSO$_4$). Concentration in vacuo afforded 8.7 g (89%) of 3-bromo-5-hydroxy-benzonitrile.

EXAMPLE 1

3-Chloro-5-[6-chloro-2-fluoro-3-(4-methyl-5-oxo-4,5-dihydro-1H-[1,2,4]triazol-3-ylmethoxy)-phenoxy]-benzonitrile; formate salt (I-2; SCHEME A)

step 1—Solid KOtBu (9.7 g, 1.05 equiv) was added to a solution of A-1 (Ar=3-chloro-5-cyano-phenyl, 12.7 g, 83 mmol) in THF (350 mL) at 0° C. The mixture was stirred for 20 min and A-2 (10 mL, 1.05 equiv) was added. The solution was warmed to RT and aged for 2 h. The mixture was poured into an aqueous NH$_4$Cl solution and extracted with EtOAc. The organic layer was dried (MgSO$_4$), filtered and the volatile materials were evaporated. Recrystallization of the resulting solid from MeOH afforded A-3.

step 2—To dry DMSO (125 mL) was added NaH (3.6 g of a 55% suspension, 2.1 equiv) and the resulting suspension was heated to 70° C. for 30 min. The solution was briefly removed from heating bath, and the benzaldoxime (9.5 g, 2 equiv) was added dropwise. The mixture was stirred at 70° C. for an additional 30 min. The thick yellow solution was cooled to RT, and a solution of A-3 (Ar=3-chloro-5-cyano-phenyl, 12.2 g, 39 mmol) and DMSO (100 mL) was added dropwise. The mixture was heated until the reaction solution became homogenous. The reaction mixture was stirred at RT for 2 h then poured into water. The resulting mixture was extracted with Et$_2$O, dried, filtered and evaporated to afford A-5 as a solid that could be recrystallized from MeOH (8.5 g, 70%).

step 3—To a solution of A-5 (Ar=3-chloro-5-cyano-phenyl, 0.42 g, 1.4 mmol) and A-6 (0.41 g, 1 equiv) in acetone was added K$_2$CO$_3$ (0.22 g, 1.2 equiv) and the reaction mixture was heated to 60° C. After 2 h, the reaction mixture was poured into a H$_2$O/EtOAc mixture, and the aqueous layer was extracted with EtOAc. The combined organic layers were dried (MgSO$_4$), filtered, and concentrated. The material was purified by SiO$_2$ chromatography eluting with a MeOH/DCM gradient (0% to 5% MeOH) to afford 0.42 g (65%) of A-7a.

step 4—A suspension of electrolytic Fe (0.19 g, 5 equiv), NH$_4$Cl (0.18 g, 5 equiv), and A-7a (0.32 g, 0.66 mmol) in EtOH (7 mL) and H$_2$O (7 mL) was heated at reflux for 5 h. The reaction mixture was filtered through CELITE® and the cake was washed with DCM. The layers were separated, and the organic layer was washed with brine, dried (MgSO$_4$), and filtered. The solution was concentrated in vacuo to afford 0.200 g (68%) of A-7b as a light brown solid.

step 5—The diazotization and chlorination was carried out as described in step 5 of example 3 except CuBr$_2$ and LiBr were replaced with CuCl$_2$ and LiCl, respectively to afford A-7c (Ar=3-chloro-5-cyano-phenyl).

step 6—Acetic anhydride (0.05 mL, 1.8 equiv) was added to a solution of the A-7c (Ar=3-chloro-5-cyano-phenyl, 0.13 g, 0.28 mmol) in HOAc (2 mL), and the solution was heated to 100° C. for 16 h. The mixture was cooled to RT, concentrated, and purified by reverse-phase HPLC to afford 0.01 g (9%) of I-2.

EXAMPLE 2

3-Chloro-5-[5-chloro-2-(4-methyl-5-oxo-4,5-dihydro-1H-[1,2,4]triazol-3-ylmethoxy)-phenoxy]-benzonitrile (I-3)

To a solution of 3-chloro-5-(5-chloro-2-hydroxyphenoxy) benzonitrile (CASRN 895572-24-4, 0.070 g, 0.25 mmol) and A-6 (0.075 g, 1 equiv) in acetone (2 mL) was added K$_2$CO$_3$ (0.041 g, 1.2 equiv.) and the solution was heated to 35° C. for 1 h. The reaction mixture was poured into water and extracted with 10% MeOH/DCM. The organic layer was washed with brine, dried (MgSO$_4$), filtered and evaporated to provide the desired ether. The product from the alkylation was dissolved in HOAc (2 mL), approximately 0.06 mL of acetic anhydride were added, and the reaction mixture was heated to 100° C. for 16 hrs. The material was purified by reverse phase HPLC to afford 0.03 g (30%) of I-3.

EXAMPLE 3

3-[6-Bromo-2-fluoro-3-(4-methyl-5-oxo-4,5-dihydro-1H-[1,2,4]triazol-3-ylmethoxy)-phenoxy]-5-difluoromethyl-benzonitrile; trifluoro-acetic acid salt (I-4)

step 1—3-Difluoromethyl-5-(2,3-difluoro-6-nitro-phenoxy)-benzonitrile was prepared as described in step 1 of example 1 except 3-chloro-5-hydroxy-benzonitrile was replaced by 3-difluoromethyl-5-hydroxy-benzonitrile.

step 2—A round-bottom flask was charged with NaH (0.55 g of a 55% suspension, 2.1 equiv) and dry DMSO (20 mL) and the resulting suspension was heated to 70° C. for 30 min. The solution was briefly removed from heating bath and the benzaldoxime (1.56 g, 2 equiv) was added dropwise. The mixture was stirred at 70° C. for an additional 30 min. The thick yellow solution was cooled to RT, and a solution of A-3 (Ar=3-cyano-5-difluoromethyl-phenyl, 2.1 g, 6.4 mmol) and DMSO (10 mL) was added dropwise. The mixture was heated until the reaction solution became homogenous. The reaction mixture was stirred at RT for 2 h then poured into water. The aqueous solution was extracted with ether, dried (MgSO$_4$), filtered and evaporated afford 2.1 g (100%) of A-5 as an orange solid.

step 3—To an ice-cold solution of A-5 (Ar=3-cyano-5-difluoromethyl-phenyl, 0.59 g) and A-6 (0.55 g, 1 equiv) in acetone (6 mL) was added K$_2$CO$_3$ (0.7 g, 3 equiv). The mixture was warmed to RT and stirred for 4 h. The mixture was poured into H$_2$O and the aqueous layer was extracted with DCM. The organic layer was washed with brine, dried (MgSO$_4$), filtered, and evaporated. The isolated brown solid was purified by SiO$_2$ chromatography eluting with EtOAc/hexanes to afford 0.50 g (55%) of A-7a (Ar=3-cyano-5-difluoromethyl-phenyl).

step 4—Electrolytic iron (0.42 g, 5 equiv) was added to a solution of A-7a (0.75 g, 1.5 mmol, Ar=3-cyano-5-difluoromethyl-phenyl) in EtOH (4 mL) and H$_2$O (3 mL). The solution was heated to 100° C. for 4 h, cooled to RT, and filtered through CELITE®. The mixture was extracted with DCM, and the organic layer was dried (MgSO$_4$), filtered and evaporated. The crude product was purified by SiO$_2$ chromatograpy eluting with a MeOH/DCM gradient (0% to 10% MeOH) to afford 0.6 g (71%) of A-7b.

step 5—A round-bottom flask was charged with CuBr$_2$ (0.16 g, 1.2 equiv), LiBr (0.16 g, 3 equiv), tert-BuONO (0.09 mL, 1.3 equiv) and MeCN (3 mL) and the solution was heated to 60° C. A solution of A-7b (0.28 g, 0.6 mmol, Ar=3-cyano-5-difluoromethyl-phenyl) in MeCN (2 mL) was added dropwise, and the solution was stirred for 6 h. The mixture was cooled, quenched with 5% HCl, and extracted with EtOAc. The combined extracts were dried (MgSO$_4$), filtered and concentrated in vacuo. The crude product was purified by SiO$_2$ chromatography eluting with a MeOH/DCM gradient (0 to 2% MeOH) to afford 0.28 g (88%) of-A-7c (Ar=3-cyano-5-difluoromethyl-phenyl).

Conversion of the 5-methanesulfonyl-4-methyl-4H-[1,2,4]triazol-3-ylmethoxy substituent to I-4 was carried out as described in step 6 of example 1.

EXAMPLE 4

3-[6-Chloro-2-fluoro-3-(5-methanesulfonyl-4-methyl-4H-[1,2,4]triazol-3-ylmethoxy)-phenoxy]-5-difluoromethyl-benzonitrile (I-5)

The diazotization and chlorination was carried out as described in step 5 of example 3 except CuBr$_2$ and LiBr were replaced with CuCl$_2$ and LiCl, respectively to afford A-7c (Ar=3-cyano-5-difluoromethyl-phenyl) in 70% yield from A-7b.

step 6—A solution of A-7c (Ar=3-cyano-5-difluoromethyl-phenyl, 0.165 g, mmol) HOAc (2 mL) and acetic anhydride (0.1 mL) was heated to 100° C. for 2 days, cooled to RT, and the residue was purified by reverse phase HPLC to afford 0.025 g (17%) of 3-[6-chloro-2-fluoro-3-(4-methyl-5-oxo-4,5-dihydro-1H [1,2,4]triazol-3-ylmethoxy)-phenoxy]-5-difluoromethyl-benzonitrile (I-5).

EXAMPLE 5

5-[3-Bromo-2-fluoro-6-(4-methyl-5-oxo-4,5-dihydro-1H-[1,2,4]triazol-3-ylmethoxy)-phenoxy]-isophthalonitrile (I-7, SCHEME D)

step 1—To a solution of di-iso-propylamine (150 mL, 108.3 g, 1.07 mol) in THF (500 mL) cooled to −78° C. and maintained under a N$_2$ atmosphere was added n-BuLi (100 mL, 1.00 mol, 10M in hexanes) over a 15 min period. The resulting mixture was stirred for 30 min at −78° C. A mixture of D-1a (45 mL, 52.110 g, 0.457 mol) and chlorotrimethylsilane (130.0 mL, 111.28 g, 1.024 mol) was added at a rate which maintained the internal reaction temperature below −50° C. The solution was stirred at −78° C. for 1 h. The reaction was quenched at −78° C. by addition of 1M H$_2$SO$_4$, diluted with MTBE and the mixture was saturated with solid NaCl. The phases were separated and the aqueous phase was extracted with MTBE (300 mL). The combined organic extracts were dried (MgSO$_4$), filtered and the solvents evaporated to afford 118 g (100%) of D-1b as a white solid.

step 2—To neat bromine (76.9 mL, 1.50 mol) cooled to 0° C. in an ice bath was added portion wise solid D-1b (126.23 g, 0.500 mol) while maintaining the internal temperature between 20-45° C. (caution: exothermic). The reaction mixture was stirred at 58° C. for 2 h. After 1 h of this period had elapsed additional bromine (45.48 g) was added and the addition funnel was rinsed with cyclohexane (10 mL). The reaction mixture was cooled to 0° C. and slowly poured into ice-cold saturated NaHSO$_3$ solution. After the addition the resulting mixture was saturated with solid NaCl, extracted with MTBE (500 mL and 200 mL), dried (MgSO$_4$) and concentrated in vacuo to afford 191 g of D-1c. The reaction mixture was distilled at ca. 60 mbar which afforded 161.53 g of colorless liquid which boiled at 110° C. and contained about 11% of the monobromo derivative. The product was redistilled through a bubble ball column at ca. 50 mbar which afforded 141.3 (78.5%) of D-1c with a boiling point of 93-94° C. which was >99.6% pure.

step 3—Preparation of iso-PrMgCl.LiCl—A sample of LiCl (4.56 g, 107.6 mmol) was dried under high vacuum with a heat gun for 10 min. To the dry solid under a N$_2$ atmosphere at 23° C. was added iso-PrMgCl (53.8 mL, 107.6 mmol, 2M solution in THF) and the resulting mixture was stirred at 23° C. for 3 days.

To a solution of D-1c (1.29 mL, 10 mmol) in THF (5 mL) at 40° C. was added the iso-PrMgCl.LiCl solution (5.5 mL, 11 mmol, 2.0M in THF) at a rate that maintained the reaction temperature below −30° C. Stirring was continued at −35 to −30° C. for 1 h then warmed to −7° C. for an additional 1 h. The reaction mixture was cooled to −30° C. and DMF (1.00 mL, 13 mmol) was added in one portion (temperature rose to −23° C.) and stirring continued for 3.5 h at −25 to +15° C. The reaction mixture was poured into 1M H₂SO₄ and ice and the resulting mixture was saturated with solid NaCl and twice extracted with MTBE. The combined extracts were dried (MgSO₄), filtered and concentrated in vacuo to afford 2.17 g (98%) of D-1d as a white solid.

step 4—To a suspension of N,N'-di-tert-butyl-5-hydroxy-isophthalamide (11.11 g, 38.0 mmol) in butyronitrile (70 mL) was added K₂CO₃ (5.5 g, 39.8 mmol) and the resulting mixture was heated at 80° C. for 70 min under a nitrogen atmosphere. To the resulting mixture was added D-2a (8.0 g, 36.2 mmol) and stirring was continued at 80° C. overnight. The reaction mixture was cooled to RT, extracted with EtOAc. The combined organic extracts were washed with water and then brine. The organic extracts were dried (MgSO₄), filtered and concentrated in vacuo to afford 13.8 g (73.4%) of D-2b (Ar=N,N'-di-tert-butyl 3,5-di-carboxamido-phenyl) as a pale yellow solid step 5a—Trifluoroacetic anhydride (1.3 mL, 12 eq.) and H₂O₂ (0.24 mL, 2.5 eq.) were combined at 0° C. and stirred for 2 h. The mixture containing trifluoroperacetic acid was added to a mixture of 5-(3-bromo-2-fluoro-6-formyl-phenoxy)-N,N'-di-tert-butyl-isophthalamide from step 4 (0.4 g, 0.81 mmol) and potassium phosphate (2.2 g, 20 eq.) in DCM at 0° C. and the reaction mixture stirred for 5 h. The reaction mixture was diluted with DCM and washed sequentially with sodium bisulfite and brine. The solution containing the formate ester was concentrated in vacuo and the residue was dissolved in THF (4 mL) and a solution of LiOH.H₂O (0.43 g, 3 eq.) in H₂O (1 mL) was added to the reaction mixture and stirred for 5 h. The reaction mixture was diluted with EtOAc and washed with HCl (aqueous), water, and brine. The organic phase was dried (Na₂SO₄), filtered and evaporated to afford 0.300 g (75%) of 5-(3-bromo-2-fluoro-6-hydroxy-phenoxy)-N,N'-di-tert-butyl-isophthalamide (D-2b, Ar=3,5-di-tert-butyl-dicarboxamido-phenyl).

step 5b—To a solution of D-2b (Ar=3,5-di-tert-butyl-dicarboxamido-phenyl, 0.3 g, 0.624 mmol) and MeCN heated to 60° C. was added POCl₃ (0.29 mL, 5 eq.). The reaction mixture was heated to 70° C. for 5 h. The reaction mixture was then cooled, and H₂O was added. The mixture was filtered to provide a crude material that was then dissolved in methanol. The organic filtrate was evaporated to provide 0.080 g (35%) of D-2b (Ar=3,5-dicyano-phenyl).

steps 6 & 7—A mixture of D-2b (Ar=3,5-dicyano-phenyl, 80 mg, 0.242 mmol), A-6 (0.07 g, 1 eq.), K₂CO₃ (0.74 g, 1.2 eq.) and acetone was stirred at 35° C. for 4 h. The reaction mixture was partitioned between water and MeOH/DCM. The organic layer was washed with brine, and evaporated to yield crude material which was dissolved in HOAc (1 mL) and acetic anhydride (5 drops) and heated to 110° C. for 24 h. The reaction was cooled, water was added and the reaction was stirred at 45° C. The reaction mixture was cooled to RT extracted with EtOAc and washed with water and then NaHCO₃ and then brine. The organic layer was dried (Na₂SO₄), filtered and evaporated. The crude product was purified by SiO₂ eluting with a MeOH/DCM gradient (0 to 10% MeOH) to afford 0.020 g (19% over two steps) of I-7.

I-6 was prepared analogously except 3-(3-bromo-2-fluoro-6-hydroxy-phenoxy)-5-chloro-benzonitrile which was prepared from 3-chloro-5-hydroxy-benzonitrile and 4-bromo-2, 3-difluoro-benzaldehyde was used in place of 5-(3-bromo-2-fluoro-6-formyl-phenoxy)-N,N'-di-tert-butyl-isophthalamide.

EXAMPLE 6

3-Chloro-5-[3-ethyl-2-fluoro-6-(4-methyl-5-oxo-4,5-dihydro-1H-[1,2,4]triazol-3-ylmethoxy)-phenoxy]-benzonitrile (I-8)

A solution containing Pd(dppf)₂ (0.014 g, 0.1 eq) and DIBAL-H (0.035 mL, 0.2 eq) were combined at 0° C. in THF (0.3 mL) and stirred for 30 min. The reaction was warmed up to RT and I-6 (0.08 g, 0.17 6 mmol) was added. Diethyl zinc (1.5 eq of a 2M solution) was added dropwise and the reaction was then heated to 60° C. for 6 h. The reaction was cooled, and poured into cold aqueous NH₄Cl, and extracted into EtOAc/MeOH. The organic layer was evaporated and the crude material purified by analytical HPLC to afford 0.005 g (7%) of I-8.

EXAMPLE 7

3-Chloro-5-[5-chloro-2-(4-methyl-5-oxo-4,5-dihydro-1H-[1,2,4]triazol-3-ylmethoxy)-benzoyl]-benzonitrile (I-1)

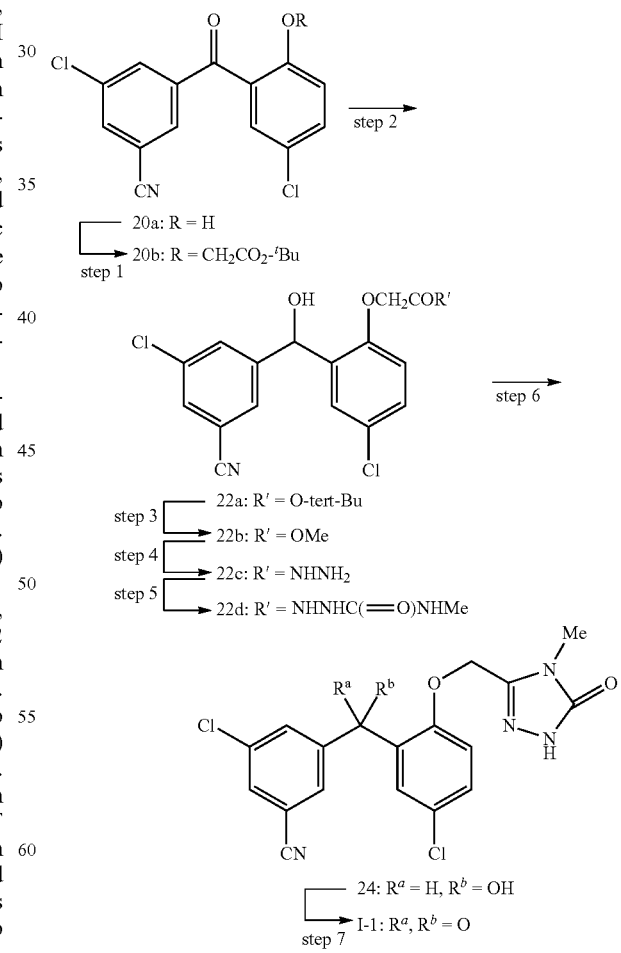

step 2—To a solution of 20b (0.55 g) in a mixture of EtOH (5 mL) and H₂O (1 mL) cooled to 0° C. was added in one portion solid NaBH₄. The solution was warmed to RT and stirred for 30 min. A solution of 5% HCl was slowly added, and the mixture was extracted with DCM. Evaporation of the volatile materials afforded 0.55 g (99%) of 22a.

step 3—To a solution of 22a (0.55 g) in DCM (6 mL) at RT was added TFA (2 mL). After stirring for 5 h, the volatile materials were evaporated and removed. The residual material was dissolved in DCM and added to a saturated aqueous solution of NaHCO₃. The solution was slowly acidified with 5% aqueous HCl and extracted with DCM. Evaporation of the volatile materials afforded the intermediate acid which was dissolved in a mixture of DCM (2 mL) and MeOH (2 mL) and a solution of trimethylsilyldiazomethane (1.0 M in hexanes) was added until a yellow color persisted. The reaction was quenched with HOAc, and the volatile materials were evaporated to afford 0.39 g (79%) of 22b.

step 4—Hydrazine (0.29 mL, 9 equiv) was added to a solution of 22b (0.38 g, 1.0 mmol) in EtOH (10 mL). The solution was heated to reflux for 5 min, cooled to RT, and stirred for 1 h. The volatile reactants were evaporated, and the residue was dissolved in DCM, washed with brine, and dried (Na₂SO₄), filtered and evaporated to afford 0.38 g (100%) of 22c.

step 5—Methyl isocyanate (0.07 mL, 1.05 equiv) was added to a solution of the 22c (0.38 g, 1.0 mmol) in dry THF (5 mL). The mixture was stirred for 30 min, and the volatile materials were removed. The material was purified by trituration with THF and DCM which afforded 0.41 g (93%) of 22d.

step 6—To a solution of 22d (0.41 g, 0.97 mmol) in tert-BuOH (9 mL) was added solid KO-tert-Bu (0.01 g, 0.1 equiv) and the solution was heated at reflux for 24 h. The solution was cooled, added to a saturated aqueous NH₄Cl solution, and extracted with EtOAc. The organic layer was washed with brine, dried (MgSO₄), filtered, and evaporated. The crude product was purified by SiO₂ chromatography eluting with a MeOH/DCM gradient to afford 0.12 g (31%) of 24.

step 7—To a solution of 24 (0.07 g, 0.17 mmol) in DCM (3 mL) was added 1,1,1-triacetoxy-1,1-dihydro-1,2-benziodoxol-3(1H)-one (Dess Martin reagent, 0.11 g, 1.5 equiv). After 1 h, SiO₂ was added to the reaction mixture, and the volatile materials were removed. The product adsorbed on SiO₂ was loaded onto a SiO₂ column and eluted with a MeOH/DCM gradient (0% to 10% MeOH) to afford 0.062 g (89%) of I-1.

EXAMPLE 8

3-{6-Bromo-2-fluoro-3-[2-(4-methyl-5-oxo-4,5-dihydro-1H-[1,2,4]triazol-3-yl)-ethyl]-phenoxy}-5-chloro-benzonitrile (I-9)

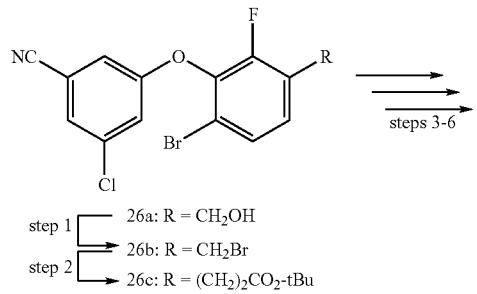

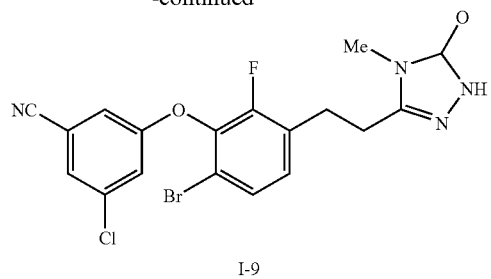

I-9 step 1—To a solution of the 26a (10 g, 28 mmol) in DCM (80 mL) cooled to 0° C. was added PBr₃ (8.35 g, 1.1 equiv) and the solution was warmed to RT. After 2 h, the reaction was slowly poured into NaHCO₃ and the aqueous layer was extracted with EtOAc. The combined extracts were dried (MgSO₄), filtered and concentrated to provide a yellow oil. This material was purified by SiO₂ chromatography eluting with hexane/EtOAc to afford 7.25 g (62%) of 26b.

step 2—To a solution diisopropylamine (1.18 mL, 1 equiv) in THF (20 mL) at cooled to 0° C. was added nBuLi (5.48 mL of a 1.6 M solution in hexanes, 1 equiv). The solution was cooled to −78° C., and a tert-BuOAc (1.18 mL, 1 equiv) was added. The solution was aged for 30 min, warmed to −50° C., and a solution of 26b (3.6 g, 8.8 mmol) in THF (10 mL) was added. The reaction mixture was slowly warmed to RT and quenched with aqueous NH₄Cl. The aqueous layer was extracted with EtOAc, and the combined organic extracts were dried (MgSO₄), filtered, and concentrated to afford 3.8 g (96%) of 26c as s yellow oil that was used without further purification.

The ester 26c was converted to the triazolone as described in steps 3 to 6 of Example 7. In step 7, evaporation of the solvent afforded 0.036 g (60%) of I-9 as a clear oil that slowly solidified.

EXAMPLE 9

2-Amino-3-methyl-butyric acid 3-[4-bromo-3-(3-chloro-5-cyano-phenoxy)-2-fluoro-benzyl]-4-methyl-5-oxo-4,5-dihydro-[1,2,4]triazol-1-ylmethyl ester, hydrochloride salt

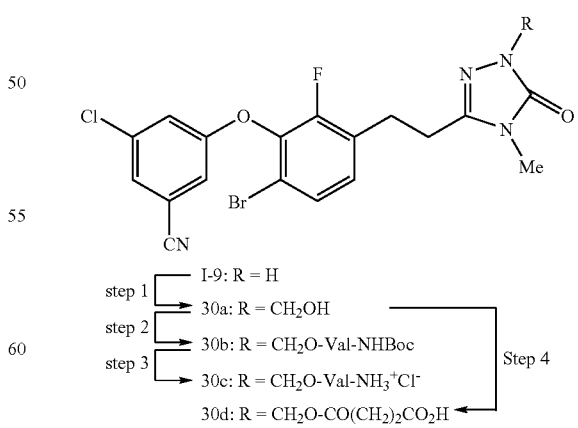

steps 1 and 2—A solution of I-9 (4.3 mmol), MeOH (90 mL) and 37% aqueous CH₂O (18 mL) is heated at reflux. After 1.5 h, the solution is cooled under a stream of nitrogen.

The reaction is concentrated and when the volume is reduced to about 30 mL, the solid precipitated and 10 g of ice is added. The solid is filtered and stored in vacuo at 50° C. overnight to afford 30a. To a solution of 30a (3.05 mmol), DMF (5 mL) is added sequentially a solution of TEA (0.2 equiv.) and DMF (1 mL) and a solution of N-Boc-valine N-carboxyanhydride (CASRN 141468-55-5, 3.66 mmol) and DMF (2 mL). The resulting solution is and stirred at RT for 2.5 h. The mixture is partitioned between water and EtOAc. The aqueous phase is extracted with EtOAc and the combined organic extracts are dried (MgSO$_4$), filtered and evaporated. The crude product can be purified by preparative TLC developed with MeOH/MeOH containing 1% TEA to afford 30b.

step 3—To a mixture of 30b and Et$_2$O maintained under an N$_2$ atmosphere is added a solution of HCl in Et$_2$O (3.5 equiv. of HCl, 1 M solution in Et$_2$O) and the resulting solution is stirred for 4 h at RT. The solid is sedimented in a centrifuge and the solvent decanted. The resulting solid is twice triturated with EtOAc/hexane and the supernatant is discarded. The solid is dried in vacuo to afford 30c.

step 4—The succinate analog is prepared as follows. The hydroxymethyl adduct 30a (3.05 mmol), succinic anhydride (3.2 mmol), DMAP (20 mg, 0.15 mmol), NMM (0.40 mL, 3.7 mmol) are dissolved in DCM (35 mL) and stirred at RT for 2.5 h. The mixture is poured into 0.5 M aqueous KHSO$_4$ and extracted with DCM. The combined extracts are dried (Na$_2$SO$_4$), filtered and evaporated to afford the crude product which is purified by filtration through a pad of SiO$_2$ eluting with a gradient (2:1 to 3:1 EtOAc/hexane then 3:1 EtOAc/hexane with 0.5% HOAc) to afford 30d.

EXAMPLE 10

3-Difluoromethyl-5-[3-ethyl-2-fluoro-6-(4-methyl-5-oxo-4,5-dihydro-1H-[1,2,4]triazol-3-ylmethoxy)-phenoxy]-benzonitrile (I-15)

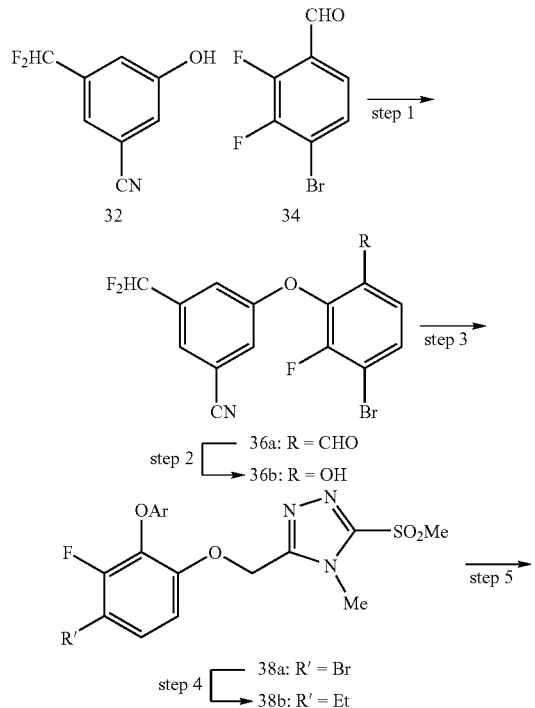

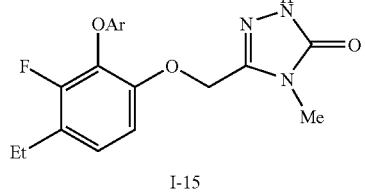

I-15

Ar = 3-cyano-5-difluoromethyl-phenyl step 1—A solution of 32 (1 g, 5.9 mmol) and K$_2$CO$_3$ (0-98 g, 7.04 mmol) in butyronitrile (15 mL) was heated to 80° C. and a solution of 34 (1.25 g, 1.25 mmol; CASRN 644985-24-0) in butyronitrile (8 mL) was added and heating was continued overnight. The reaction mixture was cooled and partitioned between H$_2$O (40 mL) and EtOAc (40 mL). The organic phase was extracted with brine and the brined layer twice extracted with EtOAc. The combined EtOAc extracts were dried (MgSO$_4$), filtered and evaporated. The crude solid was recrystallized DCM/hexane (1:1) to afford 1.24 g of 36a as a yellow solid: ms [M+H]$^+$=371.

step 2—A 50 mL flask was charged with 36a (1.24 g, 3.35 mmol), KH$_2$PO$_4$ (9.13 g, 67.1 mmol) and DCM (15 mL) and cooled to 0° C. A second flask was charged with (CF$_3$CO)$_2$ (TFAA, 4.76 mL, 10 equiv) and cooled to 0° C. under a N$_2$ atmosphere. To the TFAA was added dropwise H$_2$O$_2$ (0.4 mL, 2 equiv, 30% wt/vol in H$_2$O). The resulting trifluoroperacetic acid solution was added dropwise to the suspension containing the aldehyde and the resulting mixture stirred at 0° C. for 15 min then at RT for 4 h. The reaction was quenched with 5% sodium bisulfite (50 mL) and then DCM (50 mL) was added. The DCM extract was separated and washed with 50% brine. The brine solution was twice back-extracted with DCM. The combined DCM extracts were dried (MgSO$_4$), filtered and evaporated to afford 1.39 g of a yellow oil which still contained small amounts of 36a. The oil was dissolved in THF (12 mL), cooled to 0° C. and a solution of LiOH.H$_2$O (0.420 g) and H$_2$O (3.7 mL) was added and the resulting solution stirred for 3 h at RT. The reaction was quenched by addition of 2% HCl (5 mL), H$_2$O (30 mL) and EtOAc (30 mL). The EtOAc layer was separated and the aqueous layer extracted twice with DCM (2×25 mL). The combined organic extracts were dried (MgSO$_4$), filtered and evaporated. The resulting solid was recrystallized from DCM/hexane to afford 520 mg of 36b as a white powder. The mother liquor was further purified by preparative TLC developed with 30% EtOAc/hexane and the solid eluted from the SiO$_2$ was recrystallized to afford an additional 315 mg of 36b.

step 3—A mixture of 36b (583 mg, 1.63 mmol), 3-iodomethyl-5-methanesulfonyl-4-methyl-4H-[1,2,4]triazole (490 mg 1.68 mmol) K$_2$CO$_3$ (271 mg 2 mmol) in dry acetone (10 mL) was heated to 60° C. for 2 h. The solution was cooled to RT and partitioned between EtOAc (50 mL) and H$_2$O (50 mL). The aqueous phase was twice extracted with EtOAc (2×40 mL) and the combined EtOAc extracts were dried (MgSO$_4$), filtered and evaporated. The recovered product was triturated with hot Et$_2$O/DCM/hexanes (ca. 10/1/6) to afford 796 mg of 38a as a yellow powder: ms [M+H]$^+$=531 and 533.

step 4—An oven-dried flask was charged with 1,1'-bis-(diphenylphosphine)ferrocene Pd(II) chloride DCM complex (15.4 mg) dry THF (2 mL) and cooled to 0° C. under an Ar atmosphere. To the suspension was added DIBAL-H (0.026 mL, 1.5 M solution in toluene) and the resulting solution was stirred at 0° C. for 10 min. To the resulting solution was added a solution of 38a (0.1 g, 0.198 mmol) and dry THF (1.5 mL). The resulting solution was stirred at 0° C. for 5 min then the Et$_2$Zn (0.35 mL, 1.1 M in toluene) was added and the resulting solution heated at 60° C. for 1.5 h. The reaction mixture was cooled to RT and quenched saturated aqueous NH₄Cl (15 mL) then H₂O (20 mL) and EtOAc (30 mL) were added. The organic phase was separated and the aqueous phase extracted twice with EtOAc. The combined EtOAc extracts were dried (MgSO₄), filtered and evaporated. The crude product was purified by preparative TLC developed with 60% EtOAc/hexane and eluted to afford 135 mg of 38b as a white solid: ms [M+H]⁺=421.

step 5—To a solution of 38b (135 mg, 0.281 mmol) and glacial HOAc (2 mL) was added Ac₂O (0.05 mL) and the resulting solution was heated at 110° C. for 24 h. The reaction mixture was cooled to RT and partitioned between EtOAc (30 mL) and saturated aq. NaHCO₃ (30 mL). The biphasic mixture was stirred vigorously and separated. The EtOAc layer was washed with brine, dried (MgSO₄), filtered and evaporated. The crude product was purified on two preparative SiO₂ TLC plates developed with 80% EtOAc/hexane. The recovered product was further purified on a preparative SiO₂ TLC plated developed with 5% MeOH/DCM to afford 0.035 g of I-15 as a white powder: mp 160-161° C.; [M+H]⁺=419.

I-14 was prepared by hydrolysis of 38a utilizing the procedure described in step 5.

EXAMPLE 11

3-[3-Bromo-2-fluoro-6-(4-methyl-5-oxo-4,5-dihydro-1H-[1,2,4]triazol-3-ylmethoxy)-phenoxy]-5-ethyl-benzonitrile (I-17)

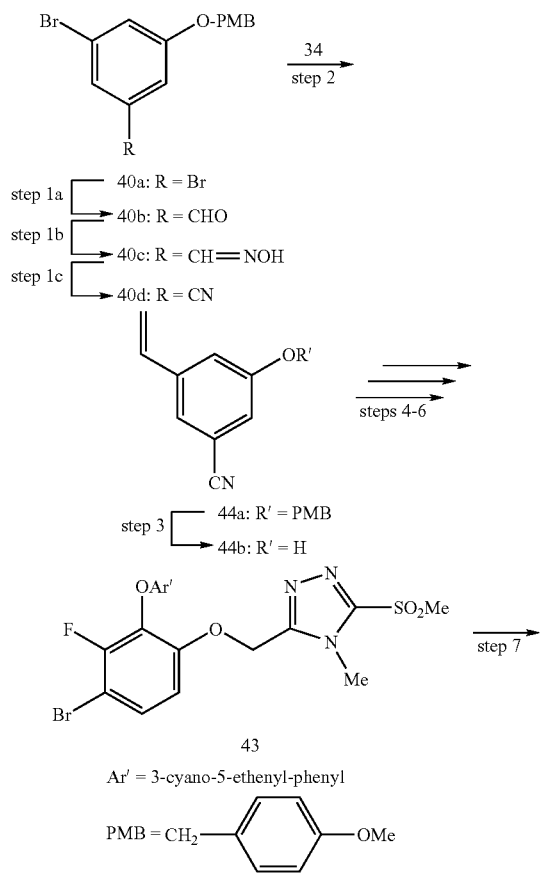

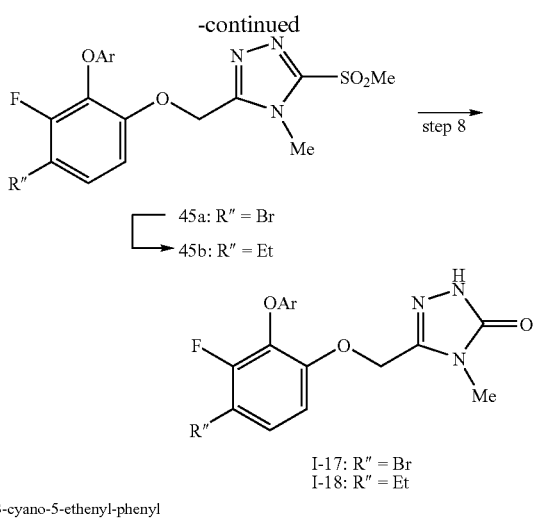

step 1a—To a solution of 1,3-dibromo-5-(4-methoxy-benzyloxy)-benzene (40a, 25 g, 67.19 mmol, CASRN 915410-934) in dry THF (100 mL) under N₂ atmosphere was added dropwise a solution of iso-propylmagnesium chloride (2M in THF) over 15 minutes. After stirring for 2.5 h, the mixture was cooled in an ice bath and quenched with dry DMF (16 mL). The solution was stirred for 30 min and then warmed to RT. The residue was partitioned between saturated aqueous NH₄Cl and Et₂O. The ether layer was separated and washed with brine. The aqueous phases were extracted with ether, the combined ether extracts were dried, filtered and evaporated to afford 21.75 g of 40b.

step 1b—To a solution of NaHCO₃ (5.86 g, 70 mmol) in water (87 mL) was added powdered hydroxylamine hydrochloride (4.88 g, 70 mmol). The above clear solution was added to a solution of 40b (21.7 g, 67 mmol) in MeOH/THF (4:1, 100 mL). The resulting mixture was stirred for 3 h. The material was condensed in vacuo to remove most of the volatile components. The residue was taken up in EtOAc and transferred to a separatory funnel. The organic phase was isolated and washed with brine solution. The aqueous phases were extracted with EtOAc. The combined EtOAc extracts were dried, filtered and evaporated to afford 24.32 g of 40c.

step 1c—To a solution of 40c (24.32 g, approx. 67 mmol) in dry dioxane (250 mL) was added pyridine (32.4 mL) followed by a slow drop wise addition of TFAA (18.7 mL). The mixture was heated under N₂ atmosphere for 4 h then cooled to RT and the concentrated in vacuo. The residue was partitioned between DCM (160 mL) and aqueous 0.5% HCl (160 mL) and transferred to a separatory funnel. The organic phase was isolated and washed with brine. The aqueous phases were extracted with DCM, combined, dried, filtered and evaporated. The product was crystallized from hot DCM/hexanes to provide 17.33 g of 40d.

step 2—A solution of 40d (6 g, 18.86 mmol), tributyl-vinyltin (6 mL, 20.74 mmol), (Ph₃P)₄P (2.15 g, 1.9 mmol) and dry toluene (70 mL) was heated at reflux for 2 h. The solvent as evaporated and the crude product was adsorbed onto a Analogix prepative hplc column (Sf-40-ISOG) and eluted with an EtOAc/hexane gradient (10 to 20% EtOAc) to afford 4.728 g of 44a as a light yellow solid.

step 3 To a solution of 44a (4.73 g, 17.8 mmol), anisole (5 mL) and toluene (28 mL) was added TFA (1.8 mL) and the resulting mixture stirred overnight at RT. The volatile components were removed on a rotovap with a bath warmed to 60°

C. The residue was taken up in EtOAc/hexane and product slowly precipitates. The product was filtered and washed with EtOAc/hexane to afford 2.04 g of 44b as a light yellow powder: [M−H]=144.

Steps 4-6 were carried out in analogously to steps 1-3 of example 10 which affords 43.

step 7—A suspension of 43 (150 mg, 0.296 mmol). $PtO_2$ (10 mL) in EtOH (5 mL) and THF (ca. 6 mL) was warmed to dissolve 43. The suspension was stirred under a $H_2$ atmosphere ($H_2$ balloon) for 1 h. The solution is filter through a CELITE pad which was washed to MeOH/THF. The solvents were evaporated in vacuo to afford 0.161 g of 45a as a light yellow solid.

step 8—was prepared from 45a using an analogous procedure to step 5 in example 10 to afford I-19; Anal. Calcd for $C_{18}H_{16}N_4O_3BrF$: C, 51.02; H, 3.61; N, 12.53. Found: C, 50.89; H, 3.59; N, 12.27.

I-18 was prepared by an analogous sequence except 45a was converted to 45b by a palladium catalyzed coupling with $Et_2Zn$ using the procedure in step 4 of example 10 and 45b was subjected to hydrolysis using an analogous procedure to step 5 in example 10.

EXAMPLE 12

3-Cyclopropyl-5-[3-ethyl-2-fluoro-6-(4-methyl-5-oxo-4,5-dihydro-1H-[1,2,4]triazol-3-ylmethoxy)-phenoxy]-benzonitrile (I-19)

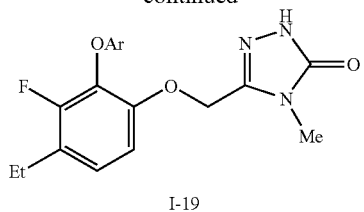

I-19

Ar = 3-cyclopropyl-5-cyano-phenyl

The olefin 46a was prepared from 44a and 34 using the procedures described in the previous examples.

step 3—To a solution of 46a (611 mg, 1.77 mmol), THF (20 mL) and $Et_2O$ (5 mL) was added $Pd(OAc)_2$ (20 mg) and the resulting solution was cooled in an ice-water bath. To this solution was added portionwise 30-40 mL of $CH_2N_2/Et_2O$ and the resulting solution was stirred for 25 min. The reaction mixture was filtered through a pad of CELITE and washed with EtOAc. The filtrate was evaporated and th cude product purified by $SiO_2$ chromatography on preparative TLC plates developed with 35% EtOAc/hexane. The $SiO_2$ was eluted to afford 500 mg of 46b as a yellow powder.

The Baeyer-Villiger oxidation, saponification of the format ester, introduction of the triazolonyl side chain and hydrolysis of the methyl sulfonyl were carried out by the analogous procedures to steps 2-5 of example 10 to afford I-18.

EXAMPLE 13

3-[3-Bromo-2-fluoro-6-(4-methyl-5-oxo-4,5-dihydro-1H-[1,2,4]triazol-3-ylmethoxy)-phenoxy]-5-(2,2,2-trifluoro-ethyl)-benzonitrile (I-20)

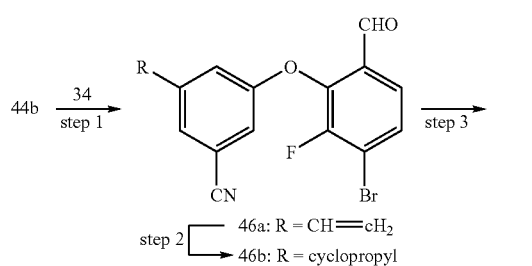

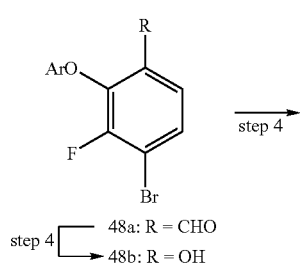

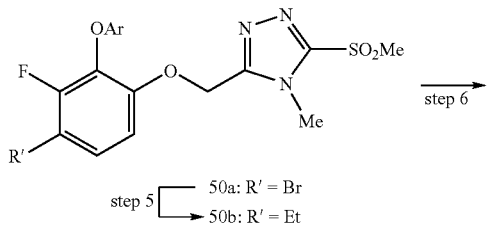

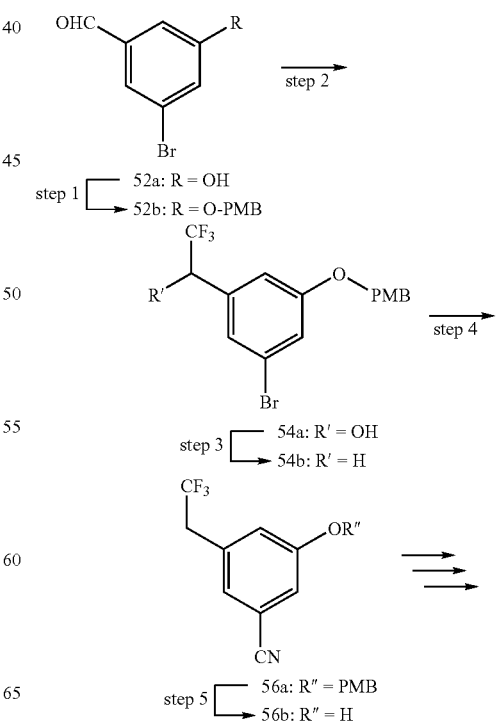

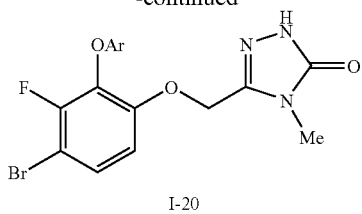

I-20

PMB = para-methoxybenzyl
Ar = 3-cyano-5-(2, 2, 2-trifluoroethyl)-phenyl step 2—To a solution of 52b (5.14 g, 16 mmol), Me₃SiCF₃ (3.75 mL, 24 mmol) and anhydrous THF (70 mL) was added Bu₄N⁺F⁻ (1.6 mL, 1.0 M in THF) and the resulting solution was stirred at 3.5 h. The pH of the solution was adjusted to ca. 2 with 2 N HCl and EtOAc (80 mL), H₂O (40 mL) and brine (60 mL) were added. The EtOAc phase was separated and the aqueous phase twice extracted with EtOAc (2×60 mL). The combined organic extracts were dried (MgSO₄), filtered and evaporated. The crude product was purified on a Analogix hplc eluting with an EtOAc/hexane gradient (0 to 29% EtOAc) which afforded 2.74 g of 54a as a yellow oil: [M–H]- 389 & 391.

step 3—To a solution of 54a (1.98 g, 5.06 mmol) and anhydrous THF (20 mL) was added thiocarbonyldiimidazole (1.4 g, 90% pure, 1.5 equiv) and the resulting solution was heated at reflux for 3 h. The reaction mixture was cooled to RT and stirred overnight. EtOAc (60 mL) and brine (80 mL) were added. The EtOAc phase was separated and the aqueous phase was twice extracted with EtOAc (2×50 mL). The combined EtOAc extracts were dried (MgSO₄), filtered and evaporated to afford 2.9 g of thiocarbamate as a golden oil. A mixture of thiocarbamate (1.0 g, 2.0 mmol), Bu₃SnH (0.79 mL. 1.5 equiv), AIBN (66 mg, 0.2 equiv) and toluene (12 mL) was heated at 85° C. for 3 h, cooled and the volatile components were evaporated. The product was purified by SiO₂ HPLC eluting with a EtOAc/hexane gradient (5 to 9% EtOAc) to afford 0.375 g of 54b: ms [M–H]=375.

step 4—A flask was charged with 54b (4.89 g, 13.69 mmol), Zn(CN)₂ (997 mg, 0.62 equiv) Pd(PPh₃)₄ (1.58 g, 0.1 equiv) and anhydrous DMF (18 mL). The flask was flushed with Ar the heated to 80° C. for ca. 15 h. The reaction mixture was cooled to RT and the DMF was removed in vacuo. The residue was taken up in EtOAc (ca. 80 mL) and washed with 2M NH₄OH (70 mL). The EtOAc phase was separated and washed sequentially with H₂O and brine. The aqueous layers were twice back-extracted with EtOAc (2×70 mL) and the combined EtOAc extracts were dried (MgSO₄), filtered and evaporated. The crude product was purified by SiO₂ HPLC by loading the dry column and eluting with an EtOAc/hexane gradient (5 to 25% EtOAc in 5% stepwise gradient) which afforded 33.35 g of 56a as a light yellow solid.

The remaining steps in the synthesis were carried out in analogy to the steps described in example 10.

EXAMPLE 14

3-[6-Chloro-2-methyl-3-(4-methyl-5-oxo-4,5-dihydro-1H-[1,2,4]triazol-3-ylmethoxy)-phenoxy]-5-chloro-benzonitrile (I-11)

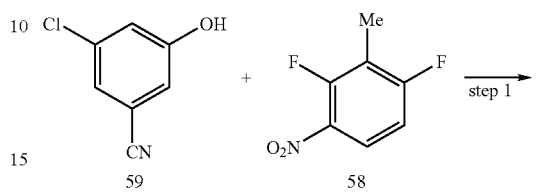

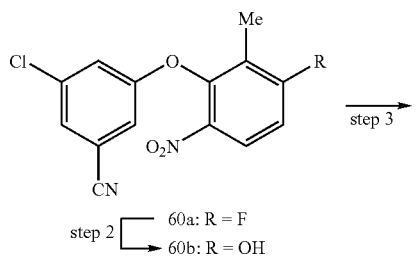

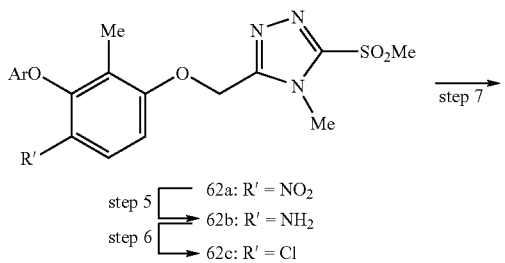

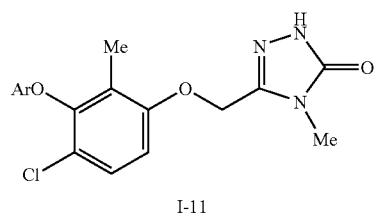

I-11

Ar = 3-chloro-5-cyano-phenyl step 1—To a solution of 59 (0.75 g, 4.9 mmol), 58 (0.86 g, 4.9 mmol), K₂CO₃ (1.01 g, 7.35 mmol) and THF (12 mL) was heated to 50° C. and stirred under a N₂ atmosphere. After 2 h one addition equivalent of K₂CO₃ was and heating continued overnight. After 22 h excess K₂CO₃ was added and the temperature raised to 70° C. After 3.5 h the solution was cooled and sat'd aqueous NH₄Cl and EtOAc were added. The EtOAc layer was separated, washed with brine, dried, filtered and evaporated to afford 1.2 g of 60a.

The synthesis of I-11 was completed following the procedures described in steps 2 to 6 of example 1.

I-21 was prepared analogously except in step 1, 58 was replaced with 3-chloro-2,4-difluoro-nitrobenzene [CASRN 3847-58-3].

EXAMPLE 15

3-{3-Bromo-2-fluoro-6-[2-(4-methyl-5-oxo-4,5-dihydro-1H-[1,2,4]triazol-3-yl)-ethyl]-phenoxy}-5-chloro-benzonitrile (I-16)

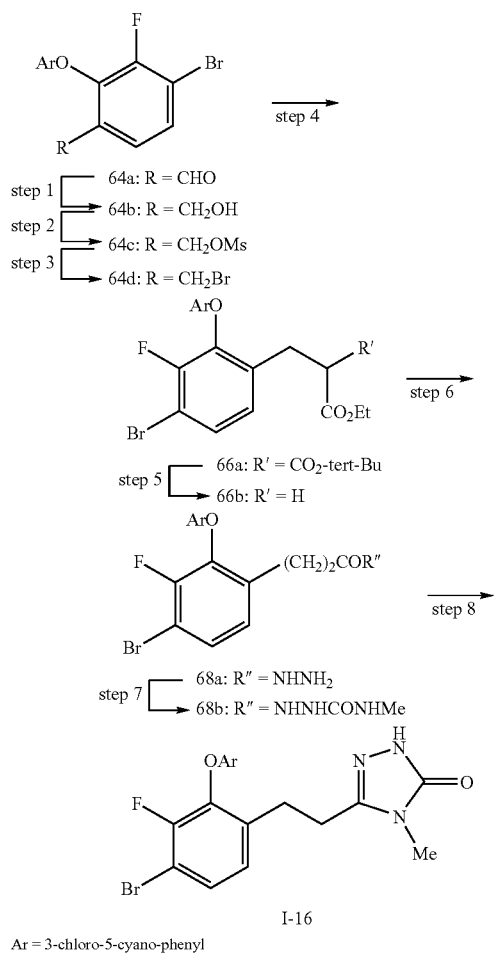

Ar = 3-chloro-5-cyano-phenyl

The starting diaryl ether 64a was prepared utilizing the procedure described in step 1 of example 10 except 32 was replaced with 3-chloro-5-hydroxy-benzonitrile.

step 1—To a solution of 64a (3.5 g, 9.87 mmol) in THF/EtOH (1:1, 36 mL) was added $NaBH_4$ (0.765 g, 20.23 mmol) and the resulting solution was stirred at RT for 2 h. The reaction was quenched with $H_2O$ and the resulting mixture extracted with EtOAc. The extract was dried, filtered and evaporated. The crude product was purified by $SiO_2$ chromatography to afford ca. 2.5 g of 64b as a white solid.

step 2—To a solution of 64b (2.5 g, 7.01 mmol) and TEA (1.7 mL, 12.27 mmol) in DCM cooled to 0° C. was added mesyl chloride (0.81 mL, 10.52 mmol). After 40 min the reaction was quenched with 5% $H_2SO_4$ (40 mL) and the resulting solution was extracted DCM and the extract washed with saturated aqueous KBr, dried, filtered and evaporated to afford 3.1 g of 64c which was used with further purification.

step 3—A solution of 64c (3.0 g, 6.881 mmol) and LiBr (1.195 g, 86.84 mmol) and THF was heated at reflux for 140 min, cooled to RT and the undissolved solids were removed by filtration. The solids were washed with DCM and acetone and the combined filtrates dried, filtered and evaporated. The crude product was purified by $SiO_2$ chromatography to afford 2.8 g of 64d as a white solid.

step 4—To a suspension NaH (0.23 g, 5.715 mmol, 60% mineral oil dispersion) and DMF cooled to 0° C. was added a solution of tert-butyl ethyl malonate (0.394 g 2.096 mmol). The solution was allowed to warm to RT. The solution was re-cooled to 0° C. and a solution of 64d (0.8 g, 1.905 mmol) and DMF was added slowly. The solution was stirred at RT for 1.75 h then quenched with sat'd. aqueous $NH_4Cl$. The reaction mixture was extracted with EtOAc and the combined extracts were washed sequentially with $H_2O$ and brine then dried, filtered and evaporated to afford 0.87 g of 66a.

step 5—A solution of 66a (0.87 g), TFA (3 mL) and DCM (3.5 mL) at 0° C. was allowed to warm to RT then heated at 70° C. overnight. The solution was cooled and the volatile solvents evaporated. The residue was dissolved in EtOAc and poured into $NaHCO_3$. The EtOAc extract was dried, filtered and evaporated. The residue was dissolved in a small amount of $H_2O$ and DMF (2 mL) was heated to 150° C. in a microwave synthesizer for about 30 min. The reaction mixture was cooled to RT and extracted with EtOAc. The extract was dried, filtered and evaporated. The residue was placed under high vacuum overnight. The crude product was purified by $SiO_2$ chromatography eluting with an EtOAc/hexane gradient (0 to 25% EtOAc) to afford 0.200 g of 66b as a colorless oil.

step 6—A solution of 66b (0.11 g, 0.258 mmol) and hydrazine (0.081 mL) in EtOH (1 mL) was heated to 78° C. After 3 h and additional 0.05 mL of hydrazine was added and after an additional 2 h the solution was cooled, and the volatile components were removed initially on a rotovap and subsequently under high vacuum. The hydrazone 68a was used without further purification.

step 7—A solution of 68a (0.1 g, 0.242 mmol) and MeNCO (0.002 g 0.362 mmol) in THF was stirred at RT for 3 h. The reaction was quenched by the addition of MeOH and evaporated to afford 0.01 g of 68b as a white solid which was used without further purification.

step 8—A solution of 68b (0.1 g, 0.213 mmol) and potassium tert-butoxide (0.0084 g, 0.75 mmol) in tert-BuOH was heated to 75° C. overnight. The reaction was cooled and poured into cold aqueous 5% HCl and the resulting mixture twice extracted with 10% MeOH/DCM. The combined extracts were washed with brine, dried filtered and evaporated to afford 0.030 g of I-16 as a white solid.

EXAMPLE 16

3-[2-Bromo-5-(4-methyl-5-oxo-4,5-dihydro-1H-[1,2,4]triazol-3-ylmethoxy)-phenoxy]-5-chloro-benzoni (I-12)

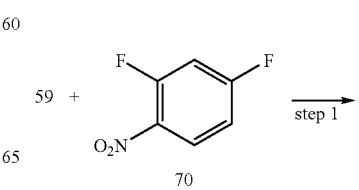

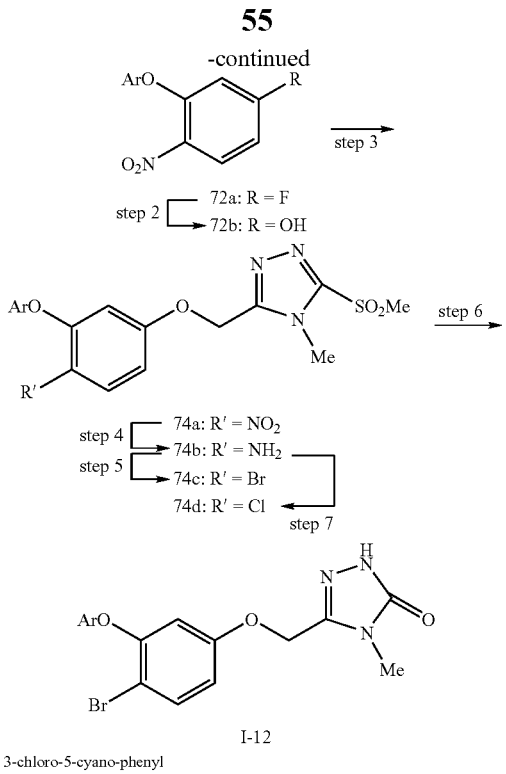

Ar = 3-chloro-5-cyano-phenyl step 1—To a solution of 59 (7.0 g, 45.58 mmol) and THF (95 mL) cooled to 0° C. was added dropwise a solution of potassium tert-butoxide (54.7 mL, 54.7 mmol, 1M solution in THF). After the addition, the reaction mixture was allowed to warm to RT and stirred for 1 h, then re-cooled to 0° C. and a solution of 70 (7.25 g, 45.58 mmol) and THF (8.6 mL) was added and the resulting heterogeneous solution was allowed to warm to RT then heated to 50° C. for 2 h. The reaction mixture was cooled, and poured into saturated aqueous NH$_4$Cl and the mixture extracted with EtOAc. The extracts were dried (MgSO$_4$), filtered and evaporated and the resulting solid was triturated with EtOH/H$_2$O to afford 16.75 g of 72a as white solid which was used without further purification.

step 2—A suspension of NaH (3.8 g, 95.72 mmol, 60% mineral oil dispersion) in DMSO (100 mL) was heated at 70° C. until the solution was homogeneous. The flask was removed from the oil bath and benzaldehyde oxime (11.0 g, 91.164 mmol) was added which formed a yellow paste and the resulting mixture was warmed at 70° C. for an additional 0.5 h. The solution was again cooled to 0° C. and a solution of 72a (13.34 g, 45.58 mmol) and DMSO (100 mL) was added via cannula. The solution was warmed to 70° C. for 1 h at which point the yellow paste had dissolved and the reaction was complete. The reaction mixture was cooled to RT and poured into 1 M HCl to quench any excess base. The resulting solution was extracted with EtOAc and the combined ectracts were thrice washed with brine, dried (MgSO$_4$), filtered and evaporated to afford a yellow solid. The solid was triturated with Et$_2$O and the resulted solid collected by filtration to afford 6.20 g (47% over two steps) of 72b: ms [M−H]=289.

step 3—A suspension of 72b (3.27 g, 11.25 mmol), A-6 (3.387 g, 11.25 mmol) and K$_2$CO$_3$ (1.87 g, 13.49 mmol) in acetone (56 mL) was heated at 60° C. for 110 min then cooled to RT. Excess K$_2$CO$_3$ was removed by filtration and the remaining solution was partitioned between water and EtOAc. The aqueous layer was extracted with EtOAc and the combined organic extracts were dried (MgSO$_4$), filtered and evaporated to afford 74a as a yellow oil.

step 4—To a suspension of 74a (5.2 g, 11.25 mmol) in EtOH (50 mL)/H$_2$O (12 mL) was added NH$_4$Cl (2.4 g, 44.99 mmol) and iron powder (2.5 g, 44.992 mmol) and the reaction mixture was heated at 100° C. for 45 min. The reaction mixture was cooled to RT and filtered through a pad of CELITE which was rinsed with EtOAc. The queous layer was separated and extracted with EtOAc and the combined organic phases were dried (MgSO$_4$), filtered and evaporated to afford a green oil which formed 4.085 g of 74b as a green foam under high vacuum.

step 5—To a solution of CuBr$_2$ (1.78 g, 6.914 mmol), LiBr (1.8 g, 20.742 mmol) and MeCN (12 mL) warmed to 60° C. was added tert-butyl nitrite (1.2 g, 12.1 mmol). The black reaction mixture was heated at 60° C. for 25 min. A solution of 74b (3 g, 6.914 mmol) and MeCN (16 mL) was added and the reaction again heated to 60° C. for 75 min then cooled to RT, diluted with 5% aqueous HBr. EtOAc was added and aqueous phase extracted with EtOAc. The combined EtOAc extracts were washed with brine, dried (MgSO$_4$), filtered and evaporated. The crude product was purified by SiO$_2$ chromatography eluting with a MeOH/DCM gradient (3 to 5% MeOH) to afford 2.348 g of 74c (68%) as a white foam.

step 6—To a solution 74c (0.300 g, 0.604 mmol) Ac$_2$O (0.102 mL, 1.087 mmol) and HOAc (3 mL) was heated at 100° C. overnight. The reaction mixture was cooled to RT, diluted with H$_2$O and extracted with EtOAc. The combined EtOAc extracts were washed with saturated aqueous NaHCO$_3$, 1 N NaOH, dried (MgSO$_4$), filtered and evaporated. The residue was purified by SiO$_2$ chromatography eluting with a MeOH/DCM stepwise gradient (3, 4 and 5% MeOH). The recovered residue was taken up in THF (2 mL), cooled to 0° C. and a solution of LiOH.H$_2$O (0.038 g) in H$_2$O (1 mL) was added. The solution was allowed to warm to RT while stirring for 1 h, quenched with 1N HCl and the aqueous layer was extracted with EtOAc. The combined extracts were dried (MgSO$_4$), filtered and evaporated to afford 0.065 g of I-12.

EXAMPLE 17

3-[2-Bromo-5-(4-methyl-5-oxo-4,5-dihydro-1H-[1,2,4]triazol-3-ylmethoxy)-phenoxy]-5-chloro-benzonitrile (I-10)

I-10 was prepared as described for I-12 in example 16 except the bromination in step 5 was replaced by an analogous chlorination (step 7 in Example 16) as described below.

step 7—To a solution of CuCl$_2$ (0.178 g, 1.32 mmol), LiCl (0.098 g, 2.305 mmol) and MeCN warmed to 60° C. was added tert-butyl nitrite 74b (0.208 g, 2.01 mmol). The reaction mixture was heated at 60° C. for 25 min and a solution of 74b (0.50 g, 1.15 mmol) and MeCN was added. The solution was again heated to 60° C. for 2 h then cooled to RT and diluted with saturated aqueous NH$_4$Cl. The resulting mixture was extracted with EtOAc and the combined EtOAc extracts were dried (MgSO$_4$), filtered and evaporated. The crude product was purified by SiO$_2$ chromatography eluting with a MeOH/DCM gradient (3 to 5% MeOH) to afford 0.422 g (81%) of 74d as a orange foam.

step 6—To a solution 74d (0.422 g, 0.931 mmol) Ac$_2$O (0.157 mL, 1.676 mmol) and HOAc was heated at 100° C. overnight. The reaction mixture was cooled to RT and partitioned between H$_2$O and EtOAc. The organic extracts were carefully washed with sat'd NaHCO$_3$ and the combined extracts were dried (MgSO$_4$), filtered and evaporated to afford a red oil. The recovered residue was taken up in THF (2 mL), cooled to 0° C. and a solution of LiOH.H₂O (0.038 g) in H₂O (1 mL) was added. The solution was allowed to warm to RT while stirring for 1 h, quenched with 1N HCl and the aqueous layer was extracted with EtOAc. The combined extracts were dried (MgSO₄), filtered and evaporated to afford 0.0985 g of I-10.

EXAMPLE 18

3-Chloro-5-[6-ethyl-2-fluoro-3-(4-methyl-5-oxo-4,5-dihydro-1H-[1,2,4]triazol-3-ylmethoxy)-phenoxy]-benzonitrile (I-13)

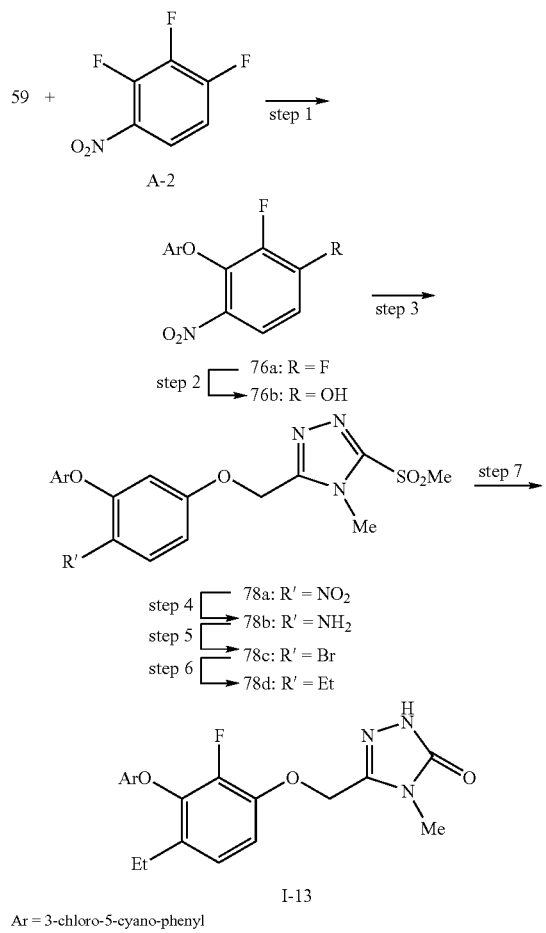

Ar = 3-chloro-5-cyano-phenyl step 1—To a solution of 59 (7.0 g, 45.58 mmol) and THF (95 mL) cooled to 0° C. was added dropwise a solution of potassium tert-butoxide (54.7 mL, 54.7 mmol, 1 M solution in THF). After the addition the reaction mixture was allowed to warm to RT and stirred for 1 h, then re-cooled to 0° C. and a solution of A-2 (7.25 g, 40.8 mmol) and THF (10 mL) was added and the resulting heterogeneous mixture was allowed to warm to RT and stir for 2 h. The solution was poured into saturated aqueous NH₄Cl and extracted with EtOAc. The combined extracts were dried (MgSO₄) filtered and evaporated to afford a viscous yellow oil. The crude product was purified by SiO₂ chromatography eluting with 15% EtOAc/hexane to afford 6.203 g (44%) of 76a Steps 2-5 were carried out analogously to the procedures steps 2-5 of example 16 which ultimately afford 78c step 6—To a solution of 78c (1 g, 1.939 mmol) and THF (6 mL) was added sequentially Pd(dppf)Cl₂.DCM (0.158 g, 0.194 mmol), diethylzinc (3.53 mL, 3.88 mmol, 1.1 M solution in toluene) and 2-dimethylamino-ethanol (0.039 mL, 0.388 mmol) and the reaction mixture was heated at 60° C. for 1 h. The reaction mixture was cooled and poured into saturated aqueous NH₄Cl and extracted with EtOAc. The combined extracts were washed with brine, dried (MgSO₄), filtered and evaporated. The crude product was purified by SiO₂ chromatography eluting with a MeOH/DCM stepwise gradient (3, 5 and 10% MeOH) to afford 0.779 (86%) of 78d.

step 2—A solution of 78d (0.779 g, 1.676 mmol), acetic anhydride (0.471 mL, 5.0 mmol) and HOAc (4 mL) was heated at 100° C. overnight. The solvent was evaporated and the residue partitioned between EtOAc and saturated aqueous NaHCO₃. The EtOAc phase was dried, filtered and evaporated. The residue was treated with LiOH.H₂O (0.211 g) in H₂O (1.5 mL) for 1 h at RT. The basic solution was acidified with 1 NHCl and extracted with EtOAc. The organic extract was dried filtered and evaporated. The residue was purified by SiO₂ chromatography eluting with 5% MeOH/DCM. The recovered product was further purified on a preparative SiO₂ TLC plate developed with a 1:1 solution of DCM and DCM/MeOH/NH₄OH (60:10:1) which afforded 0.129 g of I-13.

EXAMPLE 19

HIV-1 Reverse Transcriptase Assay

RNA-dependent DNA polymerase activity was measured using a biotinylated primer oligonucleotide and tritiated dNTP substrate. Newly synthesized DNA was quantified by capturing the biotinylated primer molecules on streptavidin coated Scintillation Proximity Assay (SPA) beads (Amersham). The sequences of the polymerase assay substrate were: 18 nt DNA primer, 5'-Biotin/GTC CCT GTT CGG GCG CCA-3'; 47 nt RNA template, 5'-GGG UCU CUC UGG WUA GAC CAC UCU AGC AGU GGC GCC CGA ACA GGG AC-3'. The biotinylated DNA primer was obtained from the Integrated DNA Technologies Inc. and the RNA template was synthesized by Dharmacon. The DNA polymerase assay (final volume 50 µl) contained 32 nM biotinylated DNA primer, 64 nM RNA substrate, dGTP, dCTP, dTTP (each at 5 µM), 103 nM [³H]-dATP (specific activity=29 µCi/mmol), in 45 mM Tris-HCl, pH 8.0, 45 mM NaCl, 2.7 mM Mg(CH₃COO)₂, 0.045% Triton X-100 w/v, 0.9 mM EDTA. The reactions contained 5 ul of serial compound dilutions in 100% DMSO for IC50 determination and the final concentrations of DMSO were 10%. Reactions were initiated by the addition of 30 µl of the HIV-RT enzyme (final concentrations of 1-3 nM). Protein concentrations were adjusted to provide linear product formation for at least 30 min of incubation. After incubation at 30° C. for 30 min, the reaction was quenched by addition of 50 µl of 200 mM EDTA (pH 8.0) and 2 mg/ml SA-PVT SPA beads (Amersham, RPNQ0009, reconstituted in 20 mM Tris-HCl, pH 8.0, 100 mM EDTA and 1% BSA). The beads were left to settle overnight and the SPA signals were counted in a 96-well top counter-NXT (Packard). IC₅₀ values were obtained by sigmoidal regression analysis using GraphPad.

EXAMPLE 20

Antiviral Assay Method

Anti-HIV antiviral activity was assessed using an adaptation of the method of Pauwels et al. (*J. Virol. Methods* 1988

20:309-321). The method is based on the ability of compounds to protect HIV-infected T lymphoblastoid cells (MT4 cells) from cell-death mediated by the infection. The endpoint of the assay was calculated as the concentration of compound at which the cell viability of the culture was preserved by 50% ('50% inhibitory concentration', $IC_{50}$). The cell viability of a culture was determined by the uptake of soluble, yellow 3-[4,5-dimethylthiazol-2-yl]-2,5-diphenyltetrazolium bromide (MTT) and its reduction to a purple insoluble formazan salt. After solubilization, spectrophotometric methods were employed to measure the amount of formazan product.

MT4 cells were prepared to be in logarithmic-phase growth and a total of $2 \times 10^6$ cells infected with the HXB2-strain of HIV at a multiplicity of 0.0001 infectious units of virus per cell in a total volume of between 200-500 microliters. The cells were incubated with virus for one hour at 37° C. before removal of virus. The cells are then washed in 0.01 M phosphate buffered saline, pH 7.2 before being resuspensed in culture medium for incubation in culture with serial dilutions of test compound. The culture medium used was RPMI 1640 without phenol red, supplemented with penicillin, streptomycin, L-glutamine and 10% fetal calf serum (GM10).

Test compounds were prepared as 2 mM solutions in dimethyl sulphoxide (DMSO). Four replicate, serial 2-fold dilutions in GM10 were then prepared and 50 microliters amounts placed in 96-well plates over a final nanomolar concentration range of 625-1.22. Fifty microliters GM10 and $3.5 \times 10^4$ infected cells were then added to each well. Control cultures containing no cells (blank), uninfected cells (100% viability; 4 replicates) and infected cells without compound (total virus-mediated cell death; 4 replicates) were also prepared. The cultures were then incubated at 37° C. in a humidified atmosphere of 5% $CO_2$ in air for 5 days.

A fresh solution of 5 mg/mL MTT was prepared in 0.01 M phosphate buffered saline, pH 7.2 and 20 microliters added to each culture. The cultures were further incubated as before for 2 hours. They were then mixed by pipetting up and down and 170 microliters of Triton X-100 in acidified isopropanol (10% v/v Triton X-100 in 1:250 mixture of concentrated HCl in isopropanol). When the formazan deposit was fully solubilized by further mixing, the absorbance (OD) of the cultures was measured at 540 nm and 690 nm wavelength (690 nm readings were used as blanks for artifacts between wells). The percent protection for each treated culture was then calculated from the equation:

$$\% \text{ Protection} = \frac{(OD \text{ drug treated cultures}) - (OD \text{ untreated virus control cultures})}{(OD \text{ uninfected cultures}) - (OD \text{ untreated virus control cultures})} \times 100\%$$

The $IC_{50}$ can be obtained from graph plots of percent protection versus $\log_{10}$ drug concentration. IC50 data for representative compounds are listed in TABLE II.

TABLE II

| Compound | Antiviral Assay IC50 (vM) |
|---|---|
| I-2 | 0.0015 |
| I-4 | 0.0007 |

EXAMPLE 21

Pharmaceutical compositions of the subject Compounds for administration via several routes were prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound according to formula IIa wherein:

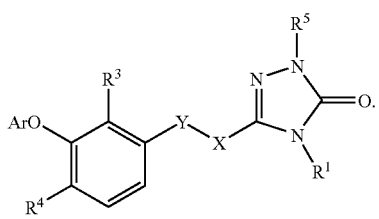

(IIa)

X is $CH_2$;
Y is $CH_2$ or O;
$R^1$ is hydrogen or $C_{1-6}$ alkyl;
$R^3$ and $R^4$ are independently hydrogen, halogen, $C_{1-6}$ alkyl, $C_{1-6}$ alkoxy or $C_{3-5}$ cycloalkyl;
$R^5$ is hydrogen, $CH_2OH$, $CH_2OC(=O)(CH_2)_nC(=O)OH$, $CH_2OC(=O)C_{1-6}$ alkyl where n is 2 to 5, or $CH_2OC(=O)CHR^{5a}NH_2$ where $R^{5a}$ is phenyl or $C_{1-6}$ lower alkyl;
Ar is phenyl substituted with 1 to 3 groups independently selected from halogen, cyano, $C_{1-6}$ haloalkyl, $C_{3-5}$ cycloalkyl or $C_{1-6}$ alkyl; or,
pharmaceutically acceptable salts thereof.

2. A compound according to claim 1 wherein:
$R^3$ is fluoro;
$R^4$ is halogen, $C_{1-6}$ alkyl or $C_{3-5}$ cycloalkyl; and,
$R^5$ is hydrogen.

3. A compound according to claim 2 wherein
Y is O;
Ar is a moiety of formula (i) wherein $R^6$ is cyano and $R^7$ is halogen, cyano or $C_{1-6}$ haloalkyl;

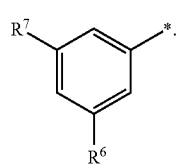

(i)

4. A compound according to claim 2 wherein both X and Y are $CH_2$ and Ar is a moiety of formula (i) wherein $R^6$ is cyano and $R^7$ is halogen, cyan or $C_{1-6}$ haloalkyl;

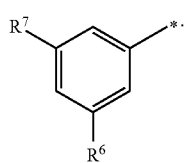

(i)

5. A compound according to claim 1 wherein:
$R^3$ is fluoro;
$R^4$ is halogen, $C_{1-6}$ alkyl or $C_{3-5}$ cycloalkyl; and,
$R^5$ is $CH_2OC(=O)(CH_2)_nC(=O)OH$ where n is 2 to 5.

6. A compound according to formula IIb wherein:

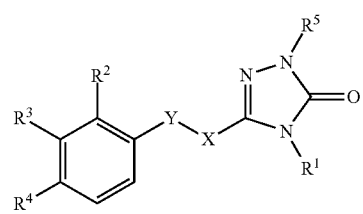

(IIb)

X is $CH_2$;
Y is $CH_2$ or O;
$R^1$ is hydrogen or $C_{1-6}$ alkyl;
$R^2$ is $C(=O)Ar$ or OAr;
$R^3$ and $R^4$ are independantly hydrogen, halogen, $C_{1-6}$ alkyl, $C_{1-6}$ alkoxy or $C_{3-5}$ cycloalkyl;
$R^5$ is hydrogen, $CH_2OH$, $CH_2OC(=O)(CH_2)_nC(=O)OH$, $CH_2OC(=O)C_{1-6}$ alkyl where n is 2 to 5, or $CH_2OC(=O)CHR^{5a}NH_2$ where $R^{5a}$ is phenyl or $C_{1-6}$ lower alkyl;
Ar is phenyl substituted with 1 to 3 groups independently selected from halogen, cyano, $C_{1-6}$ haloalkyl, $C_{3-5}$ cycloalkyl or $C_{1-6}$ alkyl; or,
pharmaceutically acceptable salts thereof.

7. A compound according to claim 6 wherein Y is O.

8. A compound according to claim 7 wherein Ar is a moiety of formula (i) wherein $R^6$ is cyano and $R^7$ is halogen, cyano or $C_{1-6}$ haloalkyl;

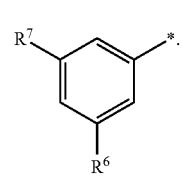

(i)

9. A compound according to claim 6 wherein, $R^2$ is $C(=O)$Ar; $R^3$ and $R^4$ are independently hydrogen, halogen or $C_{1-6}$ alkyl; Y is O; and $R^5$ is hydrogen.

10. A compound according to claim 9 wherein Ar is a moiety of formula (i) wherein $R^6$ is cyano and $R^7$ is halogen, cyano or $C_{1-6}$ haloalkyl;

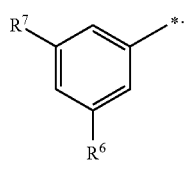

(i)

11. A compound according to claim 10 wherein $R^3$ is halogen and $R^4$ is halogen or $C_{1-6}$ alkyl.

12. A compound according to claim 1 wherein said compound is of formula (III)

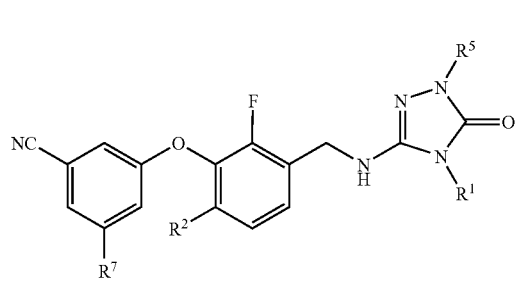

wherein:
R¹ is hydrogen or $C_{1-6}$ alkyl;
R² is hydrogen, halogen, $C_{1-6}$ alkyl, $C_{1-6}$ alkoxy or $C_{3-5}$ cycloalkyl;
R⁵ is hydrogen, $CH_2OH$ or $CH_2OC(=O)(CH_2)_2C(=O)OH$;
R⁷ is halogen, cyano or $C_{1-6}$ haloalkyl; or,
a pharmaceutically acceptable thereof.

13. A compound according to claim 12 wherein R⁵ is hydrogen.

14. A pharmaceutical composition comprising a therapeutically effective quantity of a compound according to claim 1 and at least one carrier, excipient or diluent.

* * * * *